US007282215B2

(12) United States Patent
Chowdhary et al.

(10) Patent No.: US 7,282,215 B2
(45) Date of Patent: *Oct. 16, 2007

(54) SUPPORTS FOR PHOTOSENSITIZER FORMULATIONS

(75) Inventors: Rubinah K. Chowdhary, Vancouver (CA); David Dolphin, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/851,606

(22) Filed: May 8, 2001

(65) Prior Publication Data

US 2002/0061330 A1 May 23, 2002

Related U.S. Application Data

(60) Provisional application No. 60/202,640, filed on May 8, 2000.

(51) Int. Cl.
*A61K 9/127* (2006.01)
*A61K 9/14* (2006.01)

(52) U.S. Cl. ...................... 424/450; 424/489

(58) Field of Classification Search ............... 424/450, 424/9.6, 9.5, 484, 1.21, 9.321, 9.51; 428/402.2; 264/4.1, 4.3, 4.6; 514/937
See application file for complete search history.

(56) References Cited

U.S. PATENT DOCUMENTS

| 4,125,503 A | * | 11/1978 | McCarty et al. ............ 523/402 |
| 4,229,360 A | * | 10/1980 | Schneider et al. ........... 264/4.6 |
| 4,744,989 A | | 5/1988 | Payne et al. ................. 424/490 |
| 4,883,790 A | | 11/1989 | Levy et al. .................. 540/145 |
| 4,920,143 A | | 4/1990 | Levy et al. .................. 514/410 |
| 5,095,030 A | | 3/1992 | Levy et al. .................. 514/410 |
| 5,096,629 A | | 3/1992 | Nanba et al. ................. 264/4.1 |
| 5,171,741 A | | 12/1992 | Dougherty .................. 514/185 |
| 5,171,749 A | | 12/1992 | Levy et al. .................. 514/410 |
| 5,173,504 A | | 12/1992 | Dougherty .................. 514/410 |
| 5,283,255 A | | 2/1994 | Levy et al. .................. 514/410 |
| 5,308,608 A | | 5/1994 | Dolphin et al. ................ 424/9 |
| 5,389,378 A | * | 2/1995 | Madden |
| 5,399,583 A | | 3/1995 | Levy et al. .................. 514/410 |
| 5,405,957 A | | 4/1995 | Tang et al. .................. 540/472 |
| 5,512,675 A | | 4/1996 | Tang et al. .................. 540/472 |
| 5,616,342 A | * | 4/1997 | Lyons ......................... 424/450 |
| 5,674,468 A | * | 10/1997 | Klaveness et al. ........... 424/9.3 |
| 5,703,230 A | | 12/1997 | Boyle et al. ................. 540/145 |

(Continued)

FOREIGN PATENT DOCUMENTS

WO  WO87/07502  12/1987

(Continued)

OTHER PUBLICATIONS

Alexandridis and Hatton, Colloids and Surfaces (1995) 96:1-46.

(Continued)

*Primary Examiner*—Gollamudi S. Kishore
(74) *Attorney, Agent, or Firm*—Morrison & Foerster LLP

(57) ABSTRACT

The invention is generally related to the field of formulating medicaments in association with a solid support. Such formulations comprising photosensitizers, and their use in photodynamic therapy, are also provided. Methods for the production of the medicament formulations are also disclosed.

24 Claims, 2 Drawing Sheets

U.S. PATENT DOCUMENTS

| | | | |
|---|---|---|---|
| 5,726,304 A | 3/1998 | Tang et al. | 540/145 |
| 5,831,088 A | 11/1998 | Dolphin et al. | 540/474 |
| 5,880,145 A | 3/1999 | Sternberg et al. | 514/410 |
| 5,883,246 A | 3/1999 | Brückner et al. | 540/145 |
| 5,885,557 A * | 3/1999 | Lentini | |
| 5,919,923 A | 7/1999 | Brückner et al. | 540/145 |
| 5,929,105 A | 7/1999 | Sternberg et al. | 514/410 |
| 5,939,453 A * | 8/1999 | Heller et al. | 514/452 |
| 6,015,576 A * | 1/2000 | See et al. | 424/450 |
| 6,028,066 A * | 2/2000 | Unger | |
| 6,074,666 A * | 6/2000 | Desai | |
| 6,176,842 B1 * | 1/2001 | Tachibana et al. | 604/22 |
| 6,258,378 B1 * | 7/2001 | Schneider et al. | 424/450 |
| 6,375,930 B2 * | 4/2002 | Young | |
| 6,693,093 B2 * | 2/2004 | Chowdhary et al. | 514/185 |

FOREIGN PATENT DOCUMENTS

| | | |
|---|---|---|
| WO | WO97/35559 | 10/1997 |
| WO | WO93/13943 | 3/1999 |
| WO | WO99/18998 | 4/1999 |
| WO | WO 01/32146 | 5/2001 |
| WO | WO 01/85212 | 11/2001 |
| WO | WO 02/00194 | 1/2002 |

OTHER PUBLICATIONS

Alexandridis et al., Macromolecules (1994) 27:2414-2425.

Alison et al., Photochem. Photobiol. (1990) 52(3):501-507.

Bodmeier et al., Pharm. Res. (1995) 12(8):1211-1218.

Chow and Bernard, J. Pharm. Sci. (1980) 70, 8, 924-926.

Collect et al., J. Pharm. Pharmacol. (1979) 31(Suppl.):P80.

Edsman et al., Eur. J. Pharm. Sci. (1998) 6:105-112.

Geran et al., Canc. Chemother. Reports, Part 3, 3:1-112.

Hunter et al., Aids Research and Human Retroviruses (1994) 10(Suppl.2):S95-S98.

Kabanov et al., J. Contr. Rel. (1998) 22:141-158.

Kataoka et al., J. Controller Release (1993) 24:119-132.

Krishna et al., Journal (1998) 52, 6, 331-336.

Melik-Nubarov et al., FEBS Lett. (1999) 446(1):194-198.

Mosmann, J. Immunol. Meth. (1983) 65:55-63.

Redmond and Gamlin, Photochem. Photobiol. (1999) 70(4):391-475.

Richter et al., Proc. SPIE (1993) 2078:293-304.

Rudel, Biochem. J. (1974) 139:89-95.

Schmolka, in Tarcha (Ed.) Polymers for Controlled Drug Delivery, CRC Press, Boca Raton, Florida (1991) Ch. 10, pp. 189-214.

Siggel et al., J. Phys. Chem. (1996) 100(12):2070-2075.

Wurster, J. Amer. Pharm. Assoc. (1959) 48:451.

* cited by examiner

SUPPORTS FOR PHOTOSENSITIZER FORMULATIONS

RELATED APPLICATION

This application claims benefit of priority from U.S. Provisional Application No. 60/202,640, filed May 8, 2000, which is hereby incorporated in its entirety as if fully set forth.

FIELD OF THE INVENTION

The invention is generally related to the field of formulating medicaments for thera peutic, industrial or other uses. In particular, the formulation of photosensitizers for photodynamic therapy is detailed. The photosensitizers are in the form of stabilized formulations that have been deposited on or enclosed in solid supports that permit rapid and improved hydration of the formulations. The formulations may be hydrated for use in photodynamic therapy.

BACKGROUND OF THE INVENTION

The physico-chemical characteristics of medicaments play a critical role in determining the range of their potential applications. Hydrophobic medicaments, for example, but may require appropriate formulation for use in a hydrophilic biological environment.

In the case of photosensitizing drugs, the majority of them that are of pharmaceutical interest for photodynamic therapy (PDT) are based on the tetra- or polypyrrolic structure, which are hydrophobic in character. Their effectiveness relies on their association with cellular membranes, thereby being able to target highly sensitive membranous intracellular organelles that control critical metabolic functions. The hydrophobic character of the photosensitizers means that they cannot be administered directly to a hydrophilic environment due to a tendency to aggregate (by molecular stacking, precipitation or other mechanisms), which can severely curtail photosensitization processes (Siggel et al. *J. Phys. Chem.* 100(12):2070-2075, December 1996). Thus they require formulation in carriers which are able to provide a hydrophobic environment to maintain them in a non aggregated form in both the formulation and in aqueous preparations prior to use. For photosensitizers such as porphyrin- and benzoporphyrin (green porphyrin) derivatives, the tendency to undergo aggregation has been found to be high.

The photosensitizer benzoporphyrin derivative monoacid-ring A (BPD-MA, Verteporfin®, QLT PhotoTherapeutics Inc., Vancouver, BC, Canada) has been successfully formulated using liposomes as a carrier. Liposomal preparations containing porphyrin photosensitizers are described in allowed U.S. application Ser. No. 08/489,850 filed Jun. 13, 1995, which is incorporated herein in its entirety by reference. Liposomal BPD-MA was originally manufactured on a large scale using the conventional thin film technique where the drug and lipids are dissolved in a volatile organic solvent in a round bottom flask and deposited as a film as the solvent is removed by rotary evaporation. The film is then hydrated using an iso-osmolar solution of lactose to produce large multilamellar vesicles (MLVs). These undergo a size reduction process using homogenization prior to filter sterilization, packaging and lyophilization to produce a final pharmaceutical product. Both the thin film production and hydration processes were found to be problematic for large scale manufacturing.

An alternative process to thin film suitable for large-scale manufacturing is the "Presome" technology (U.S. Pat. No. 5,096,629). Briefly, the method involves pumping superheated organic solutions of phospholipids into a large evacuated sterile chamber. This process removes the organic solvent and results in lipid powder. The photosensitizer BPD-MA, phospholipids, and antioxidants are dissolved in methylene chloride to produce presome powder. The presome powder is then hydrated using lactose monohydrate solution, followed by microfluidization, filter-sterilization and then lyophilization. In this process, lactose solution has been used as an iso-osmolar agent for hydrating the thin film or presome powder before lyophilization. The presome powder yields a similar final product to that of the conventional thin film method. Therefore presome technology has the advantage of being suitable for large scale production but has similar limitations and numerous step requirements as described for the thin film. Yet another process is based on the formation of a "proliposome" (see U.S. Pat. No. 4,744,989 and WO 87/07502) which could reduce the number of steps in the manufacture of liposomal photosensitizers.

The synthesis of BPD-MA normally results in equimolar quantities of A-ring and B-ring intermediates. The B-ring compounds are effective photosensitizers, but further development for PDT treatment using these compounds has been limited by their greater tendency to undergo self-aggregation and their lower solubility compared to A-ring compounds. Aggregation results in inefficient delivery of drug to plasma proteins on injection into the blood stream and poor performance in vivo. It also poses a greater formulation challenge as B-ring compounds have been shown to undergo aggregation within the bilayer in liposomal formulations. The use of various homopolymeric systems e.g. polyvinylpyrrolidones (PVPs) and polyethylene glycols (PEGs) have also proved unsuccessful in preventing aggregation in B-ring compounds.

Formulations using biocompatible block copolymers are receiving increasingly wider usage in the pharmaceutical industry for enhancing drug solubility and bioavailability (reviewed by Schmolka, Chapter 10, pp189-214, in Tarcha (Ed.) *Polymers for Controlled Drug Delivery*, CRC Press, Boch Raton, Fla., 1991; Alexandridis & Hatton, Colloids and Surfaces 96:1-46, 1995)). Poloxamers are an example of block copolymers found to be useful in this area. These are symmetrical compounds of the A-B-A type composed of a central PPO (polypropylene oxide) with flanking PEO (polyethylene oxide) blocks on both sides. The PPO block provides the hydrophobic interaction with the drug to be stabilized.

There is a continuing need in the art for alternative formulations and processing methods which will allow the preparation of photosensitizer drug formulations, with a minimum number of steps, and in a form which is suitable for storage, as well as rapid hydration or reconstitution to produce a form suitable for therapeutic use. Preferably, methods should also be amenable to large-scale production.

SUMMARY OF THE INVENTION

The present invention provides compositions and methods directed to improved photosensitizer formulations that meet many of the needs in the art. These improvements are particularly advantageous in preparing photosensitizer formulations, for use in photodynamic therapy (PDT). More specifically, the compositions and methods are directed to the association of a precursor formulation containing a photosensitizer and a carrier agent with at least one solid support material. Thus if the solid support material is present in a solvent precursor mixture containing photosensitizer and carrier agent, the mixture becomes physically associated with the solid support upon solvent removal. Any order of addition, between photosensitizer, carrier agent and solid support, to said solvent is permitted by the invention. Subsequent addition of an aqueous based medium rapidly hydrates the precursor formulation to produce a formulation containing complexes of photosensitizer and carrier agent. These complexes may be of any form, including (but not limited to), stable micelles, emulsions, gels, matrices, transition phases between the defined states, vesicles or other carrier forms suitable for use in photodynamic therapy.

Thus the invention provides compositions that contain photosensitizer and carrier agent associated with a solid support. The invention also provides methods for formulating photosensitizers by use of a carrier agent and a solid support material on which a photosensitizer and carrier mixture is deposited. These formulations may then be rapidly hydrated to produce a hydrated formulation of photosensitizer and carrier in which the two are in complexes. The invention further provides methods of using hydrated complexes of photosensitizer and carrier in any manner relating to photosensitizer use, such as administration to subjects undergoing photodynamic therapy.

DETAILED DESCRIPTION OF THE INVENTION

Figure 1:
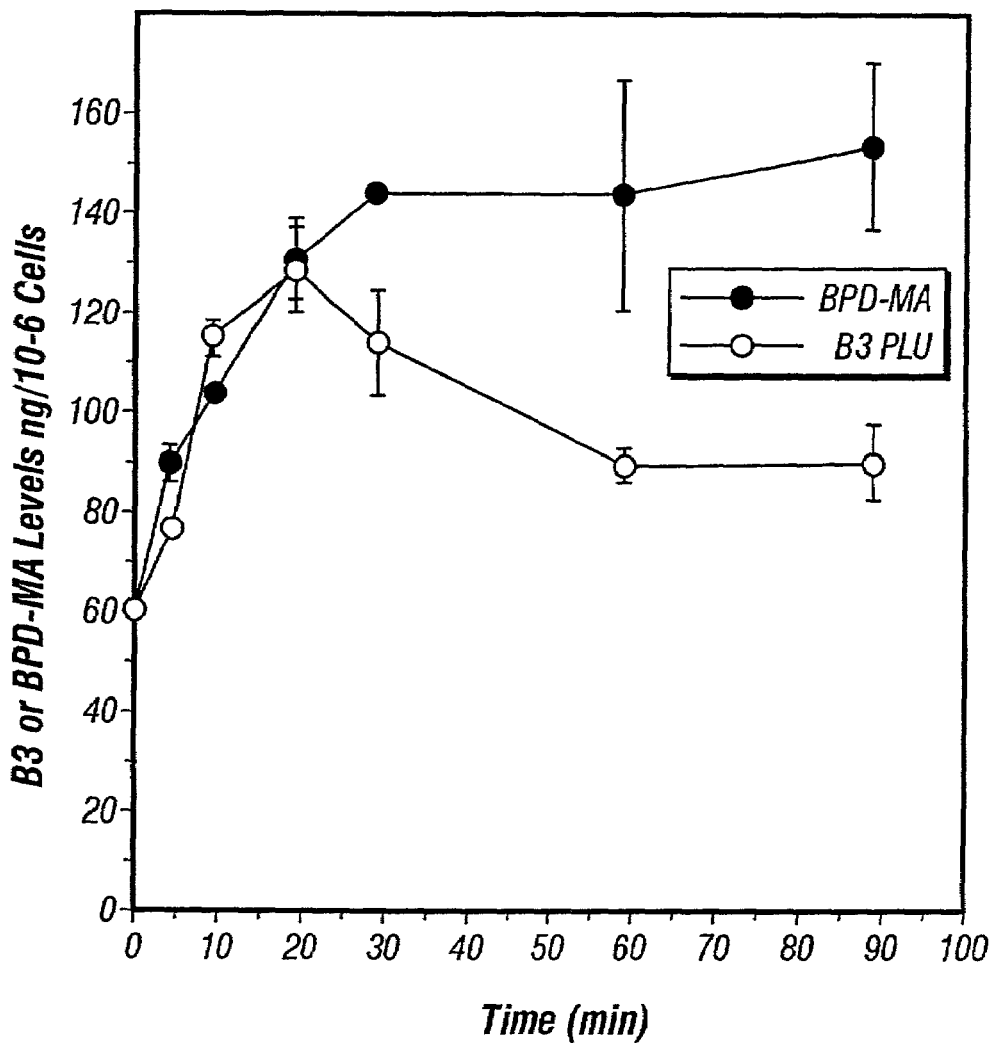
FIG. 1 is a graphical representation of in vitro cellular uptake of the photosensitizer B-B3 using block copolymer and liposomal formulations. Uptake of copolymer Pluronic® P123 formulation was very rapid compared to BPD-MA liposomal formulation. 50% uptake level was observed to be close to 'zero' incubation time, with uptake of B-B3 peaking at around 20 min. In comparison, BPD-MA achieved saturation level at 30 min, with 50% uptake at approximately 5 min.

Prior to setting forth the invention, it may be helpful to an understanding thereof to first set forth definitions of certain terms that will be used hereinafter.

"Medicament" is defined as any hydrophobic or hydrophilic material suitable for pharmaceutical or therapeutic use. Preferably, the medicaments of the invention are biologically active. More preferably, they are photosensitizers as described below. Additional examples of medicaments of the invention include, but are not limiting to, drugs, vaccines, adjuvants, contrasting agents, proteins, carbohydrates, supplements, and vitamins.

"Block copolymer" and "copolymer" refer to carriers and carrier agents comprising any variation of two or more covalently linked blocks. The copolymers may be symmetric or asymmetric, amphiphilic (containing both hydrophilic and hydrophobic chemical groups), graft, or random. The blocks are linked by any appropriate linkage, including, but not limited to, —$CH_2$—, —O—, —NH—, carbonyl, ester, amide, and imide linkages. The carriers may or may not be charged, and preferably comprise two or three blocks. Preferably, the copolymers are symmetric or non-symmetric type triblock copolymers, which may be represented as A-B-A and A-B-A', respectively.

The carriers of the invention include poloxamers, or "PEO-PPO-PEO", which are symmetrical triblock copolymers of polyoxyethylene (PEO, EO) and polyoxypropylene (PPO, PO) denoted as PEO-PPO-PEO or $(EO)_{n1}(PO)_m(EO)_{n2}$ or $HO(C_2H_4O)_a(C_3H_6O)_b(C_2H_4O)_cH$. These copolymers are commercially available and have been well characterized in the art. Examples are the poloxamers sold under various trademarks, such as Pluronic® (BASF Corp.) or Synperonics® (ICI).

Also within the scope of the invention are amphiphilic copolymers as described in WO 99/18998 (or its corresponding U.S. patent, if any), which is hereby incorporated by reference in its entirety as if fully set forth. Explicitly excluded from inclusion for use alone as a "block copolymer" or "copolymer" of the invention, however, is an amphiphilic polymer of polystyrene sodium sulphonate and vinyl naphthalene when the photosensitizer used in the invention is 5, 10, 15, 20 tetrakis phenyl porphyrin. This specific amphiphilic polymer may also be excluded from inclusion for use alone when other photosensitizers are used in the invention. Thus 5, 10, 15, 20 tetrakis phenyl porphyrin may be used in the invention if other copolymers or other photosensitizers or medicaments are used. In addition to copolymers, carriers and carrier agents of the invention include lipid compounds capable of forming or being associated with liposomes. In applications of the invention relating to liposome preparation, the associated or incorporated medicament is preferably limited either to photosensitizers or the use of exosupports. Carriers of the invention may be in a "liquid form", which includes any liquid or liquefied form of the carrier. Examples of the "liquid form" of carriers are the carriers dissolved in solution and the carrier in a liquefied form, such as in melted or molten forms. Preferred dissolved forms are prepared by solubilizing copolymers in appropriate solvents, preferably volatile solvents.

After formulation with a medicament of interest, and in the presence of a solid support, the carrier may be converted to a "solid form" by removal of solvent or otherwise solidification of the carrier. Solvent removal may be by any means known in the art, including, but not limited to, spray drying, lyophilization, heating, and application of a vacuum. Solidification, especially of carriers in a liquefied form, may be by any means known in the art. These include, but are not limited to, cooling or hardening in the presence of a medicament or solid carrier.

"Complex" and "complexes" refer to stable micellar, emulsion, gel, matrix or transition phases between the defined states formed when a block copolymer and a medicament or photosensitizer associate to result in such forms. In some instances, formulation of such complexes requires the presence of additional agents that participate in the formation of micellar, emulsion, gel, matrix or transition phase structures in solution. Examples of such agents include oils or other lipids. The complexes of the invention may optionally include pharmaceutically acceptable excipients. They may also include adjuvants.

"Green porphyrins" refer to porphyrin derivatives obtained by reacting a porphyrin nucleus with an alkyne in a Diels-Alder type reaction to obtain a mono-hydrobenzoporphyrin.

"Solid support" or "support" refers to solid material with which a medicament (or photosensitizer) and carrier mixture may become associated. Preferably, the mixture is a precursor formulation which physically associates with the solid material of the support. In cases of the mixture being in a solvent system, the association predominantly occurs upon solvent removal. The solid materials of the invention are normally not soluble in a solvent system solubilizing the medicament (or photosensitizer) and carrier mixture. Of course combinations of solid support materials may be used in association with any medicament/carrier mixture.

In another aspect of the invention, the carrier in a molten or other liquefied form acts as a "solvent" for hydrophobic medicaments such as some photosensitizers, thus obviating the need for solvent removal for association of the solid support with the medicament/carrier mixture. Such "solvent" carriers in their molten, melted, or other liquefied form may be readily combined with a medicament of interest. Examples of particularly excellent combinations using a "solvent" carrier as solvent include poloxamers or polyethylene glycols (PEGs) as the "solvent" carrier with photosensitizers. The ability to avoid extraneous solvent use is advantageous for ecological, health, safety, and disposal considerations. It is also beneficial in simplifying the processes involved (i.e. need for special precautions, handling and/or instrumentation) in preparing the compositions of the invention.

The solid supports of the invention may be defined as endo-supports and exo-supports. The solid material may be considered an endo-support if the mixture is deposited thereon. Thus the support forms the core of the composition, or particle, formed between the medicament/carrier mixture and the solid material. This is readily accomplished by using processes known in the art such as a Wurster-type process to spray the medicament/carrier mixture onto a support from an organic solvent, aqueous, or "solvent" carrier solution. Alternatively, the support can be randomly distributed, by processes known in the art such as by spray drying, within the composition or particle when solid material in a finely divided form is utilized.

If the mixture is partially or wholly enclosed by the material then it is termed an exo-support. Stated differently, solid materials can be used to encapsulate the medicament/carrier mixture, by processes such as Wurster-type or fluid bed-type coating processes, or by spin-coating processes, where the medicament/carrier mixture is co-extruded into the core of the support material which forms a capillary structure. These extruded and coated threads are then shortened into appropriate lengths for subsequent use with greater ease of hydration, which is one advantage provided by the present invention. The use of an exo-support is particularly advantageous for use with tacky or sticky carrier materials such as Pluronic® P123 or poloxamer 403, where the exo-support may permit a discreet small particle size by providing a hard coating to prevent agglomeration. This approach is also essential if a medicament and "solvent" carrier "melt" was to form the core for encapsulation. The advantages of this approach include the likelihood of enhancing the shelf life of the encapsulated medicament. It should be clear from the above, however, that a vessel used to contain the medicament (or photosensitizer) and carrier mixture is not considered an exo-, or endo-, support of the invention.

Both endo- and exo-supports of the invention may be further classified as injectable and non-injectable based upon whether the medicament/carrier mixtures containing said support may be injected into a subject after solvation and/or hydration with an aqueous solution. Examples of injectable combinations include medicament/carrier mixtures deposited on an endo-support or encapsulated by an exo-support material that is biocompatible and water soluble. A preferred endo-support of this type are carbohydrate crystals such as trehalose or lactose.

Examples of non-injectable combinations include medicament/carrier mixtures deposited on an endo-support or encapsulated by an exo-support material that is not biocompatible and/or not soluble. Upon solvation and/or hydration, the support material is removed to permit either further processing or immediate use of the medicament and carrier mixture. Preferably, removal of the support material is before the medicament and carrier mixture is supplied for clinical or pharmaceutical applications. An example of further processing is the production of single dosage forms of the medicament and carrier mixture by converting it into a solid form. Of course in the absence of hydration, non-injectable combinations may be used by other clinical means, such as conversion to oral or topical formulations by combination with further excipients.

Generally, endo- or exo-support materials that produce an injectable combination after solvation and/or hydration are biocompatible materials which might be natural humectants suitable for the particular mode of administration. A humectant is defined as any material not soluble in organic solvents or "solvent" carriers (carrier "melts") and able to sequester water and/or increase water binding capacity and/or content. Humectants can be either soluble or insoluble in aqueous solutions, but when insoluble, they are nevertheless hydratable.

For injection via intravenous administration, for example, the material should be suitable for injection, non-toxic at the dosages administered, and metabolizable by the subject's body. Exemplars of such materials include biopolymers such as carbohydrates, such as mono-, di-, tri- and polysaccharides (i.e. starches and cellulose); salts; amino acids; and derivatives (i.e. alcohol, acid, carbonyl, alkyl, acyl, aryl, amine, fatty acid, lipid, phosphoryl, deoxy, etc.) of the above, such as aminoglycosides. Alternatively, the materials can be synthetic polymers tailored to the specific need but nevertheless biodegradable or otherwise excretable by a subject's body. These include polymeric compounds and block copolymers such as poloxamers. Thus the injectable combinations of the invention may be either soluble or insoluble in the presence of an aqueous solution.

Soluble combinations of a medicament/carrier mixture and solid support form solutions upon solvation and/or hydration. "Insoluble" combinations include those that form suspensions and/or emulsions upon solvation and/or hydration. Examples of solid supports that result in such "insoluble" combinations include liposomes, polymers that form nanoparticles, unimolecular micelles, or other similar structures with particle sizes suitable for injection. Of course injectable combinations, whether soluble or "insoluble", may also be suitable for non-injection delivery modes, including oral, topical and ocular administration. The solid materials used in such embodiments of the invention may or may not interact or contribute to stabilization of the medicament or the medicament/carrier composition.

Endo- or exo-support materials that produce a non-injectable combination are preferably readily removable after solvation and/or hydration, by well known processes such as filtration, centrifugation, etc., to allow further processing, packaging or use of the medicament and carrier mixture. In the absence of further processing, medicament/carrier mixture and solid support combinations that are non-injectable, whether soluble or insoluble upon solvation and/or hydration, may of course still be suitable for non-injection delivery modes, including oral, topical and ocular administration.

Solid support materials that result in non-injectable and insoluble medicament/carrier mixtures upon solvation and/or hydration may be further classified as hydratable or non-hydratable depending on the characteristics of the support material used. Examples of support materials that are hydratable include, but are not limited to, insoluble polymers of biological or synthetic origin such as agarose beads, cellulose, and natural or synthetic humectant materials. Examples of support materials that are non-hydratable include, but are not limited to, glass or Teflon coated beads. Without being bound by theory, hydratable supports may be of particular advantage by providing additional interfaces for hydration of the associated medicament/carrier mixture.

The compositions and methods of the invention may also serve to prepare a medicament in a "non-aggregated" form defined as that in which a medicament (i.e. photosensitizer) does not exhibit sufficient strong intermolecular interactions with other medicament molecules to result in significant aggregation.

The present invention provides compositions and methods which utilize the presence of a solid support material to permit deposition or encapsulation of a medicament and a carrier agent from a liquefied or solubilized form. The deposited or encapsulated material may be in any form. The compositions permit and the methods include rapid hydration of the deposited or encapsulated mixture of medicament and carrier. Upon hydration, the medicament and carrier is in the form of a complex for use in any appropriate application requiring the medicament. In the case of photosensitizers as the medicament, the use is preferably as part of photodynamic therapy (PDT). For the majority of the remaining description, "photosensitizer" will be used as the exemplary medicament without limiting the full scope of the invention.

Preferably, the solid support material of the invention is present in a mixture of photosensitizer and carrier (precursor formulation) in a solvent prior to deposition or encapsulation upon solvent removal. The solvent is preferably volatile. After deposition or encapsulation, the mixture may be rapidly hydrated with an aqueous based medium to form photosensitizer-carrier complexes. The actual forms of these complexes may include, but are not limited to, micelles, emulsions, gels, matrices, transition phases between the defined states, vesicles, liposomes or other forms suitable for use in photodynamic therapy (PDT).

The compositions and methods of the invention advantageously produce photosensitizers in a form either suitable for immediate use or readily processed to an immediately useable form. For example, hydration of medicament and carrier agent from the solid support containing formulations of the invention may produce complexes that are ready for use. Alternatively, the solid support containing formulations of the invention may be further formulated prior to hydration. Yet another alternative is further processing of the formulation to reduce its particulate size. Such processing may occur either before or after hydration of the formulation.

The following describes the photosensitizers, methods of administration, compositions, formulations and storage and handling of the present invention. Experimental data are also presented and described.

A. Photosensitizers

The invention may be practiced with a variety of synthetic and naturally occurring pyrrole based photosensitizers, this includes pro-drugs such as 5-aminolevulinic acid, porphyrins and porphyrin derivatives e.g. chlorins, bacteriochlorins, isobacteriochlorins, phthalocyanine and naphthalocyanines and other tetra- and poly-macrocyclic compounds, and related compounds (e.g. pyropheophorbides, sapphyrins and texaphyrins) and metal complexes (such as, but not limited by, tin, aluminum, zinc, lutetium). Tetrahydrochlorins, purpurins, porphycenes, and phenothiaziniums are also within the scope of the invention.

Particularly preferred photosensitizers include green porphyrins such as BPD-MA, EA6 and B3. Generally, any polypyrrolic macrocyclic photosensitive compound that is hydrophobic can be used in the invention. Examples of these and other photosensitizers for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine;

berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'- tetramethyl-1'-thioangelicin; and 4,6,4',5'-tetramethyl angelicin. Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyriliun perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopy rilium hexofluoro phosphate, 2,6-bis(1,1-dimethyl-ethyl)-4-[1-[2,6-bis(1,1-dimethyl-ethyl) selenopyran-4-ylidene]-3-propenyl ]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl -ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2, 6-bis(1,1dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-diethyl-ethyl) selenopyran-4-ylidene]-4-(2-butenyl)]-; selenopyrilium hexofluoro phosphate, 2,6-bis(1,1-dimethyl-ethyl)4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[2-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis (1,1-dimethyl-ethyl)-4-[1-[2,6-bis(1,1-dimethyl-ethyl) telluropyran-4-ylidene]-3-propenyl]-. Exemplary chlorins dyes include 5-azachlorin dimethyl ester derivative; 5, 10, 15, 20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2, 18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylesterz; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo [3,2-g] [1] benzopyran-2-one; 2H-selenolo[3,2-g] [1] benzothiopyran-2-one; 7H-selenolo[3,2-g] [1] benzoselenopyran-7-one; 7H-selenopyrano[3,2-f] [1] benzofuran-7-one; 7H-selenopyrano[3,2-f] [1] benzo-thiophene-7-one; 2H-thienol[3,2-g] [1] benzopyran-2-one; 7H-thienol[3,2-g] [1] benzothiopyran-7-one; 7H-thiopyrano[3,2-f] [1] benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2-18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminster-fullerene; [1-methyl-succinate-4-methyl-cyclohexadiene-2, 3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin mesotetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2"3"'-q)porphyrazine; zinc (II) 2-(3-pyridyloxy)benzo[b]-10,19,28-tri(1,1-dimethylethyl)trinaphtho[2',3'-g:2"1::2"',3"'-q] porphyrazine; zinc (II) 2,18-bis-(3-pyridyloxy)dibenzo[b,1]-10,26-di(1,1-dimethyl-ethyl)dinaphtho[2',3'-g:2"',3"'-q] porphyrazine; zinc (II) 2,9-bis-(3-pyridyloxy)dibenzo[b,g]-17,26-di(1,1-dimethyl-ethyl)dinaphtho[2",3'-1:2"',3"'-q] porphyrazine; zinc (II) 2,9,16-tris-(3-pyridyloxy) tribenzo [b,g,1]-24=(1,1-dimethyl-ethyl)naphtho[2"',3'-q] porphyrazine; zinc (II) 2,3-bis-(3-pyridyloxy) benzo[b]-10,19,28-tri(1,1-dimethyl-ethyl)trinaphtho[2',3'-g:2",3"1:2"', 3"'-q]porphyrazine; zinc (II) 2,3,18,19-tetrakis-(3-pyridyloxy) dibenzo[b,1]-10,26-di(1,1-dimethyl -ethyl)trinaphtho[2',3'-g:2"',3"'-q]porphyrazine; zinc (II) 2,3,9,10-tetrakis-(3-pyridyloxy) dibenzo[b,g]-17,26-di(1,1-dimethyl-ethyl)dinaphtho[2",3'-1:2"',3"'-q]porphyrazine; zinc (II) 2,3,9,10,16,17-hexakis-(3-pyridyloxy)tribenzo[b,g,1]-24-(1,1-dimethyl-ethyl)naphtho[2"',3"'-q]porphyrazine; zinc (II) 2-(3-N-methyl)pyridyloxy)benzo[b]-10,19,28-tri(1,1-dim-ethyl-ethyl)trinaphtho[2',3'-g:2",3"1:2"',3"'-q]porphyrazine monoiodide; zinc (II) 2,18-bis-(3-(N -methyl)pyridyloxy) dibenzo[b,1]-10,26-di(1,1-dimethylethyl)dinaphtho[2',3'-g:2"',3"'-q]porphyrazine diiodide; zinc (II) 2,9-bis-(3-(N-methyl)pyridyloxy)dibenzo[b,g]-17,26-di(1,1-dimethylethyl) dinaphtho[2",3'-1:2"',3"'-q]porphyrazine diiodide; zinc (II) 2,9,16-tris-(3-(N-methyl-pyridyloxy)tribenzo[b,g,1]-24-(1, 1-dimethylethyl)naphtho[2"',3"'-q]porphyrazine triiodide; zinc (II) 2,3-bis-(3-(N-methyl)pyridyloxy)benzo[b]-10,19, 28-tri(1,1-dimethylethyl)trinaphtho[2',3'-g:2",3"-1:2"',3"'-q] porphyrazine diiodide; zinc (II) 2,3,18,19-tetrakis-(3-(N-methyl)pyridyloxy)dibenzo[b,1]-10,26-di(1,1-dimethyi) dinaphtho[2',3'-g:2"',3"'-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3'-1:2"',3"'-q] porphyrazine tetraiodide; zinc (II) 2,3,9,10,16,17-hexakis-(3-(N-methyl)pyridyloxy)tribenzo[b,g,1]-24-(1,1-dimethylethyl)naphtho[2"',3"'-q]porphyrazine hexaiodide; zinc (II) meso-diphenyl tetrabenzoporphyrin; zinc (II) meso-triphenyl tetrabenzoporphyrin; zinc (II) meso-etrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]] phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (2) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladiun (II) tetra(t-butyl)-phthalocyanine; (diol) (t-butyl)$_3$-phthalocyanato palladium(II); ruthenium(II) dipotassiumbis(triphenyl-phosphine-monosulphonate) phthalocyanine; silicon phthalocyanine bis(tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy, zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butylchloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethylaminobenzo[a]phenothiazinium chloride; and 5-ethylamino-9-diethylaminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)] hypocrellin B; 5,8-dibromo[1,12-CHBrC(=CH$_2$)CBr(COMe)] hypocrellin B; 5,8-dibromo[1-CH$_2$COMe, 12-COCOCH$_2$Br-] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)-] hypocrellin B; 5,8-diiodo[1,12-CH$_2$C(CH$_2$I)=C(COMe)-] hypocrellin B; 2-(N,N-diethylamino) ethylaminated hypocrellin B; 3,10-bis[2-(N,N-diethylamino)-ethylamine]hypocrellin B; 4,9-bis[2-(N,N-diethyl-amino)-ethylamine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 1-hydroxy hypocrellin B or 2-hydroxy hypocrellin B; hypocrellin A; hypocrellin B; 5-iodo[1,12-CH$_2$C(CH$_2$I)=C(COMe)-] hypocrellin B; 8-iodo[1,12-CH$_2$C(CH$_2$I)=C(COMe)-] hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (¹/₁ molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18- tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienylbovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl -porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy) porphycene; 2,7,12,17-tetrakis(2-methoxyethyl)-9-[4-(β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-terakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene, 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-diethylarninomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-t-butyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetrakis-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylaminoformamide; protoporphyrin formamide; sapphyrin 13,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"-trimethylaminophenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl) porphine; tetra(4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl)porphyrin; meso-tetra(4-N-trimethylanilinium)-porphine; uroporphyrin; uroporphyrin I (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; ¾',5'-trimethyl-aza-psoralen;

4,4',8-trimethyl-5'-anino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxypsoralen; 5'-acetyl-4,8-dimethyl-psoralen; 5'-aceto-8-methyl-psoralen; and 5'-aceto-4,8-dimethyl-psoralen. Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester, rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'", 1'"-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3'", 3'"-dimethylacryloyloxymethyl)-2,2':5',2"-terthiophene; 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',2":5",2'"-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion)p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phioxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

In one embodiment the preferred compounds for formulating are the highly hydrophobic tetrapyrrolic A and B-ring compounds, such as BPD-DA, -DB, -MA, and -MB. Most preferred are the B-ring compounds, BPD-MB, B-EA6, B-B3; the A-ring compounds BPD-MA, A-EA6 and A-B3; and dihydroxychlorins.

These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used. It is preferred that the absorption spectrum of the photosensitizer be in the visible range, typically between 350 nm and 1200 nm, more preferably between 400-900 nm, and even more preferably between 600-900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

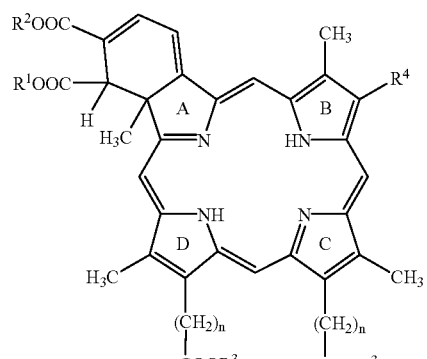

1 or

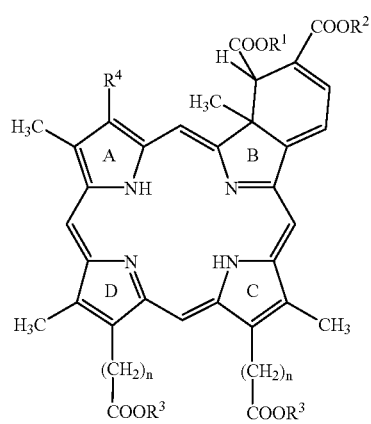

2

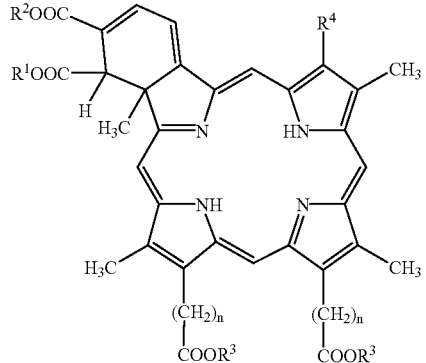

3 or

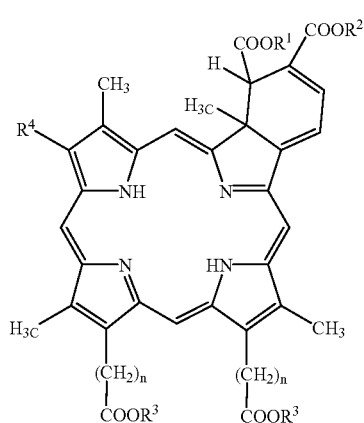

4 where $R^4$ is vinyl or 1-hydroxyethyl and $R^1$, $R^2$, and $R^3$ are H or alkyl or substituted alkyl. BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin, as well as illustrations of A and B ring forms of EA6 and B3, are as follows:

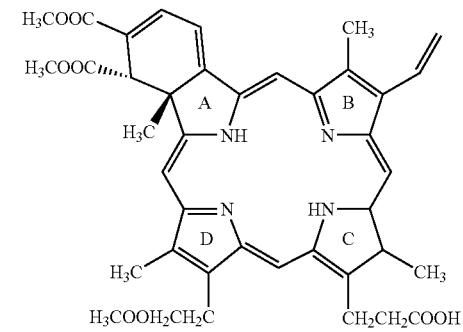

BPD-MA$_C$

-continued

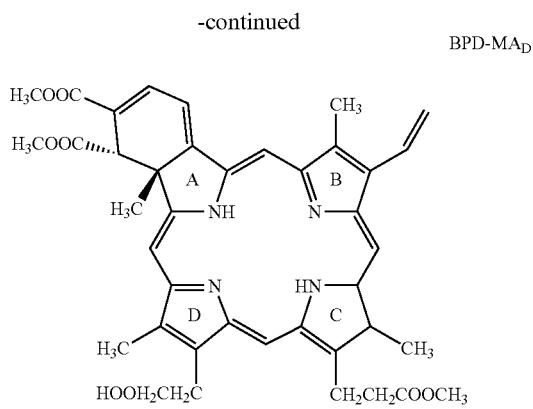
BPD-MA_D

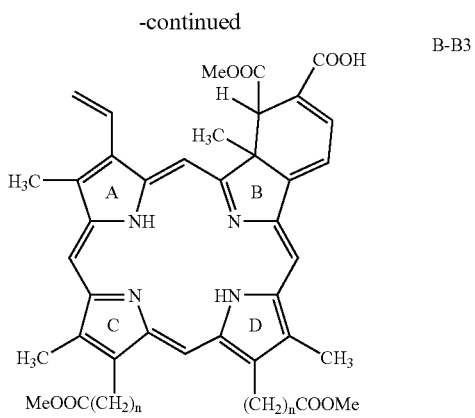
B-B3

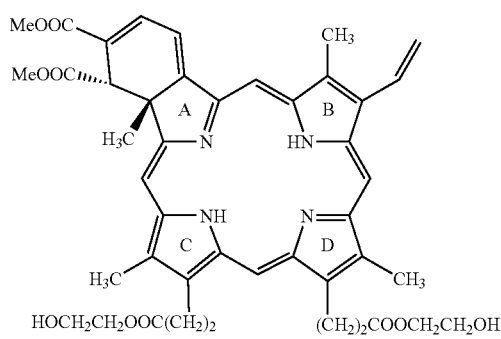
A-EA6

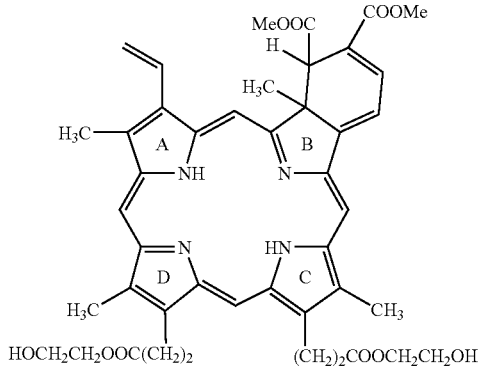
B-EA6

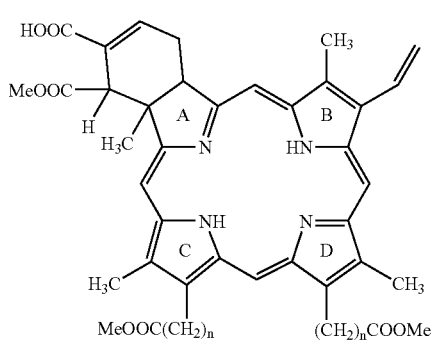
A-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Optionally excluded from inclusion as a photosensitizer of the invention, however, is 5,10,15,20 tetrakis phenyl porphyrin.

Dimeric forms of the green porphyrin and dimeric or multimeric forms of green porphyrin/porphyrin combinations may also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Other non-limiting examples of photosensitizers which may be useful in the invention are photosensitizing Diels-Alder porphyrin derivatives, described in U.S. Pat. No. 5,308,608; porphyrin-like compounds, described in U.S. Pat. Nos. 5,405,957, 5,512,675, and 5,726,304; bacteriochlorophyll-A derivatives described in U.S. Pat. Nos. 5,171,741 and 5,173,504; chlorins, isobacteriochlorins and bacteriochlorins, as described in U.S. Pat. No. 5,831,088; meso-monoiodo-substituted and meso substituted tripyrrane, described in U.S. Pat. No. 5,831,088; polypyrrolic macrocycles from meso-substituted tripyrrane compounds, described in U.S. Pat. Nos. 5,703,230, 5,883,246, and 5,919,923; and ethylene glycol esters, described in U.S. Pat. No. 5,929,105. All of the patents cited in this paragraph are hereby incorporated by reference as if fully set forth. Generally any hydrophobic or hydrophilic photosensitizers, which absorb in the ultra-violet, visible and infra-red spectroscopic ranges would be useful for practicing this invention.

Presently a number of photosensitizer drugs of interest are hydrophobic with a tetrapyrrole-based structure. These drugs have an inherent tendency to aggregate, which can severely curtail photosensitization processes (Siggel et al. J. Phys. Chem. 100(12):2070-2075, December, 1996). For example, the synthetic pathway for BPD yields A and B ring intermediates in approximately equimolar quantities, which can be derivatized further. It was found that the A-ring derivatives, such as BPD-MA (Verteporfin), could easily be formulated for delivery using traditional means, whereas B-ring compounds proved more difficult to formulate due to their tendency to undergo self-association.

In an additional aspect of the invention, the photosensitizers of the invention may be conjugated to various ligands that facilitate targeting to tissues and cells before the photosensitizers are formulated with block copolymers. These ligands include those that are receptor-specific as well as immunoglobulins and fragments thereof. Preferred ligands include antibodies in general and monoclonal antibodies, as well as immunologically reactive fragments thereof. Moreover, the block copolymer may be conjugated to the ligands to which the photosensitizer binds to facilitate improved complexing of non-hydrophobic photosensitizers with the copolymer.

Dimeric forms of the green porphyrin and dimeric or multimeric forms of green porphyrin/porphyrin combinations may also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Other non-limiting examples of photosensitizers which may be useful in the invention are photosensitizing Diels-Alder porphyries derivatives, described in U.S. Pat. No. 5,308,608; porphyrin-like compounds, described in U.S. Pat. Nos. 5,405,957, 5,512675, and 5,726,304; bacteriochlorophyll-A derivatives described in U.S. Pat. Nos. 5,171,741 and 5,173,504; chlorins, isobacteriochlorins and bacteriochlorins, as described in U.S. Pat. No. 5,831,088; meso-monoiodo-substituted and meso substituted tripyrrane, described in U.S. Pat. No. 5,831,088; polypyrrolic macrocycles from meso-substituted tripyrrane compounds, described in U.S. Pat. Nos. 5,703,230, 5,883,246, and 5,919,923; and ethylene glycol esters, described in U.S. Pat. No. 5,929,105. All of the patents cited in this paragraph are hereby incorporated by reference as if fully set forth. Generally any hydrophobic or hydrophilic photosensitizers, which absorb in the ultra-violet, visible and infra-red spectroscopic ranges would be useful for practicing this invention.

The preferred compounds of the present invention are the photosensitive compounds including naturally occurring or synthetic porphyrins, pyrroles, chlorins, tetrahydrochlorins, pyropheophorphides, purpurins, porphycenes, phenothiaziniums, pheophorbides, bacteriochlorins, isobacteriochlorins, phthalocyanines, napthalocyanines, and expanded pyrrole-based macrocyclic systems such as, sapphyrins and texaphyrins, and derivatives thereof.

The most preferred compounds of the present invention are green porphyrins ("Gps") in general and the monohydrobenzoporphyrin derivatives ("BPDs") as described in U.S. Pat. No. 5,171,749 and related U.S. Pat. Nos. 5,283,255; 5,399,583; 4,883,790; 4,920,143; 5,095,030 and 5,171,749; BPD derivative EA6 compounds are described in U.S. Pat. No. 5,880,145; and B3 compounds described in U.S. Pat. No. 5,929,105. Particularly preferred photosensitizers of the invention include BPD-MA and verteporfin®. The corresponding B ring forms of these photosensitizers are also preferred. Additional preferred photosensitizers include the B ring forms of EA6 and B3 (see FIG. 3B) as well as the corresponding A ring forms (see FIG. 3A, formula 1).

Presently a number of photosensitizer drugs of interest are hydrophobic with a tetrapyrrole-based structure. These drugs have an inherent tendency to aggregate, which can severely curtail photosensitization processes (Siggel et al. J. Phys. Chem. 100(12):2070-2075, December, 1996). For example, the synthetic pathway for BPD yields A and B ring intermediates in approximately equimolar quantities, which can be derivatized further. It was found that the A-ring derivatives, such as BPD-MA (Verteporfin), could easily be formulated for delivery using traditional means, whereas B-ring compounds proved more difficult to formulate due to their tendency to undergo self-association.

In one embodiment the preferred compounds for formulating are the highly hydrophobic tetrapyrrolic A and B-ring compounds. Most preferred are the B-ring compounds, BPD-MB, B-EA6, B-B3; the A-ring compounds BPD-MA, A-EA6 and A-B3; and dihydroxychlorins.

In an additional aspect of the invention, the photosensitizers of the invention may be conjugated to various ligands that facilitate targeting to tissues and cells before the photosensitizers are formulated with block copolymers. These ligands include those that are receptor-specific as well as immunoglobulins and fragments thereof. Preferred ligands include antibodies in general and monoclonal antibodies, as well as immunologically reactive fragments thereof More-over, the block copolymer may be conjugated to the ligands to which the photosensitizer binds to facilitate improved complexing of non-hydrophobic photosensitizers with the copolymer.

B. Carriers

The formulations of the invention may be practiced with a variety of carrier agents, including combinations of such agents. The preferred carrier agents of the invention are symmetric and asymmetric block copolymers composed of two or more blocks. These can be amphiphilic random, graft, or block copolymers, either branched or linear which can be biodegradable or otherwise excretable. The hydrophobe is the part of the copolymer that can interact with the photosensitizer. Examples include, but are not limited to, homo- or hetero-polymers composed of amino acids such as tryptophan, histidine, aspartate, or phenylalanine; pyridines, purines, or indoles; toluene, benzene and alkyl benzene, anthracene, or phenanthrene; and propylene glycol. The hydrophile can be selected from, but is not limited to, any of the following: polyethylene glycol, polyethylene oxide, poly amino acids, polycarboxylates and polysulphonates. Blocks and/or monomers within the blocks are linked by, but not limited to groups such as —CH2—, —O—, —NH—, carbonyl, ester, amide and imine linkages. More preferred are the symmetric and asymmetric block polymers of the structure A-B-A and A-B-A', respectively, where the ratio of hydrophilic to hydrophobic groups range from 1:20 to 20:1. Most preferred are those that can form micellar/mixed micelle suspensions, emulsions, gels or other stable complexes with the photosensitizer of interest. Additional carriers of the invention include lipid-containing compounds capable of forming or being associated with liposomes.

Where block copolymers are used, the copolymers are preferably water-soluble triblock copolymers of composed of polyethylene oxide (PEO), and polypropylene oxide (PPO) denoted as PEO-PPO-PEO or (EO)n1(PO)m(EO)n2 or HO(C2H4O)a(C3H6O)b(C2H4O)cH (Schmolka, Supra; Alexandridis & Hatton, Colloids and Surfaces 96:1-46, 1995). More preferred are those where a and c are independently from 1-150 units and b ranges from 10-200 units with the overall molecular weight ranging from 1,000 to 50,000 daltons. Particularly preferred are those where a equals c and b ranges from 10-200 units.

Others examples of block copolymers that are useful for this invention are those where the central block is composed of other amphiphilic, charged or uncharged monomeric groups which are likely to interact more specifically with a photosensitizer of interest (Kataoka et al. J. Controlled Release 24:119-132, 1993). These moieties are selected depending on the properties (polarity, charge, aromatic character, etc.) of the photosensitizer to be formulated.

Block copolymers that would be useful in this invention are of the non-toxic di-block, symmetric and non-symmetric triblock copolymers and dendrimer types. More preferable are the symmetrical triblock copolymers, preferably those composed of PEO-PPO-PEO types of block copolymers, where the hydrophobic PPO provides the methyl groups that are believed to interact with and stabilize the substance to be solubilized.

PEO confers water solubility to the copolymer, although the hydrogen bonding interactions of the ether oxygen with water molecules probably occurs along the entire copolymer. These copolymers are available from a number of commercial sources such as BASF Corporation (Pluronic® series) and ICI (Synperonic® series). In the numeric naming system for both the series, the last digit of the copolymer number multiplied by 10 gives the approximate percent molecular weight of the hydrophilic blocks (PEO). Poloxamers can be roughly divided into 3 main categories, all of which can be useful for stabilizing and delivery of drug substances, namely emulsion forming, micelle forming, and water soluble ones which form an extended network in solution. At higher concentrations they have a tendency to undergo gel formation under certain temperature conditions (Edsman et al. Eur J Pharm Sci. 6, 105-112, 1998). Some of the important factors which determine poloxamer characteristics and behavior in aqueous suspension are the molecular weight, PPO:PEO ratio, temperature conditions, concentration, and presence of ionic materials. There is consequently a wide range of characteristics in existing commercially available copolymers, which can be exploited for formulation purposes, whether for merely monomerization of hydrophobic photosensitizers or for controlled drug delivery purposes. Additionally, alternative PEO-PPO-PEO polymers can be tailored according to requirements of a particular drug substance e.g. molecular weight, PPO:PEO ratio, as well as administration route.

Another characteristic of the copolymers is their wetting or detergent capacity which has been used to promote plasma membrane permeability of various drugs (Melik-Nubarov et al., FEBS Lett. 5;446(1):194-198, 1999), and thereby increasing bioavailability of the drugs. It has been shown that these copolymers can also act as immunoadjuvants (Hunter et al. Aids Research and Human Retroviruses 10 (Supplement 2): S95-S98, 1994) and could improve the benefits of a regime, for example if used in conjunction with PDT particularly for autoimmune disorders.

The present invention includes the observation that block copolymers form simple complexes with photosensitizing drugs. The type of complexes formed was found to be codependent on the specific block copolymer and the specific photosensitizer utilized. These complexes may be in forms such as micellar, emulsion, gel, matrix or transition phases between the defined states.

Another observation of the invention is that certain copolymers in the poloxamer series spontaneously form micelles with the photosensitizer drug. Micellar formulations have been produced in the laboratory scale using the thin film method. For large scale drug production, the drug-copolymer and other components can be combined using techniques such as, but not limited to, spray or freeze drying, or the Wurster-type coating process (Wurster, J. Amer. Pharm. Assoc. 48:451, 1959) to form granules which will provide a higher surface area for hydration or reconstitution. When forming micelles, it is preferred that block copolymers of the above formula with a=60-80 and b=10 to 40 units in length are used.

The invention also revealed that certain copolymers in the poloxamer series spontaneously form a simple, stable bicomponent oil in water (O/W) emulsions on simply handshaking with water or osmotically balanced aqueous solutions. The emulsion particle size in these preparations is small enough for intravenous administration (filterable through 0.2 (m filtration membranes), and particle size is retained over 76 hours without any loss of drug on filtration. This, in conjunction with the knowledge that emulsions can be stabilized as reconstitutable solid state preparations, makes the preparations highly viable as formulations for hydrophobic photosensitizing drugs.

Drugs could be incorporated directly into the block copolymer as described in the Example section, or using minimal amounts of an injectable solvent. Direct dissolution of photosensitizers in poloxamers, particularly those in semi-solid or liquid form at ambient or body temperatures, would also provide useful ointments for topical and mucosal applications. Alternatively, drug dissolved in minimal amounts of a non-toxic solvent may be added to an aqueous suspension of the block copolymer if it does not interfere with drug-copolymer interactions, or destabilize the formulation in any other way.

Further, gel and matrix forming copolymers have been useful for controlled or sustained release, as well as delivery systems that can be triggered, and are prepared at higher polymer concentrations than those deemed suitable for parenteral formulations. Gelling of block copolymers at temperatures above ambient has been exploited in order to form a higher viscosity drug release reservoir in contact with the lesion, either topically or onto mucosal area be treated. This allows a relatively non-invasive spraying of medicament onto affected areas, with good contact maintained between the lesion to be treated and the drug formulation prior to light exposure.

The preferred block copolymers are those that can form stable complexes with a photosensitizer drug of interest. The more preferred copolymers are the ones that form stable emulsions and/or micelles with the photosensitizers, or undergo gel formation at body temperature. Other preferred copolymers are liquefied to permit a medicament, such as a photosensitizer, to be dissolved directly in the absence of a solvent. Poloxamers in liquid form act as highly effective solvents in which hydrophobic drugs can be directly dissolved. Examples 2 and 3 below illustrate this embodiment of the invention by demonstrating that different types of hydrophobic photosensitizers such as BPD-MA and B-B3 can be dissolved in liquefied poloxamers.

Surprisingly, it appears that the nature of the drug can also influence the characteristics of the block copolymer in aqueous solution. Block copolymers tested independently of the drug gave more viscous solutions than in the presence of the drug substance. Without being bound by theory, the reason for this observation may be due to earlier induction or promotion of micelle formation by hydrophobic interactions of the drug substance with the PPO block in the case of poloxamer. Depending on the nature of the active material, its interaction with the block copolymer might alter formulation characteristics e.g. serve to enhance formulation stability by promoting micellization or altering emulsion characteristics. It is now generally accepted that certain block copolymers do, form micelles in aqueous suspensions under certain conditions (Alexandridis et al. Macromolecules 27:2414-2425, 1994).

For parenteral administration the most preferred block copolymers are those that form micelles with the photosensitive compound in the formulation. Water-soluble drugs might also benefit from the presence of hydrophilic polymers to prevent chemical degradation, e.g. hydrolysis (Collett et al. J. Pharm. Pharmacol. 31 (suppl.) P80, 1979) during the manufacturing process, or storage, or improved ease of reconstitution in the clinic.

More preferred for parenteral micellar formulations of highly hydrophobic drugs are the family of poloxamers with the highest commercially available molecular weight of PPO (n=60-80), and those with %PEO in the 20-40% range. For more water soluble formulations, non-micelle forming, hydrophilic polymers from the entire range could be utilized (PEO=40-90%). Emulsion forming polymers (%PEO=10-20%) might be useful for certain hydrophobic and amphiphilic drugs. Poloxamers are non-hygroscopic with water content of less than 0.5% w/w on exposure to the atmosphere. Gel formation takes place in aqueous solutions in the higher molecular weight polymers and is concentration and temperature dependent. For instance, Pluronic® P123 gels at concentrations greater than 20% w/v at ambient temperature conditions. Gelling or viscosity is enhanced at body temperature, which could prove useful for prolonging contact time of topical ocular and enteral formulations with the lesions to be treated using PDT.

As an illustration of one embodiment of the invention, the block copolymer poloxamer series and in particular P123 has been extensively examined. Therefore any poloxamers or block copolymer, in general, that has similar characteristics, as P123 would be useful in this invention. Preferably, the block copolymers are effective in the concentration range of 0.005% to 20% w/v, more preferably in the range of 2 to 20% w/v for parenteral formulations, and 0-100% for topical, enteral and ocular formulations. Poloxamers in liquid form act as highly effective solvents in which hydrophobic drugs can be directly dissolved. Poloxamers in liquid or paste form at ambient temperatures can be employed as liquids or ointments for application.

P123 has been shown to be highly effective for formulating a range of tetrapyrrolic hydrophobic drug substances, such as the A, B, C and D ring compounds. In the Example section below, formulation of the following A-ring compounds: BPD-MA, A-EA6, A-B3; B-ring compounds; B-EA6, and B-B3; and other photosensitizers such as dihydroxychlorins and pyropheophorbides, with P123 illustrate the versatility of this particular block copolymer. This includes A-ring compounds such as BPD-MA where block copolymers could be used to formulate an alternative product to a concentration as high as 4 mg/ml in 10% P123, and also A-EA6 and A-B3, all of which formulate very readily. B-ring compounds have lower drug loading characteristics, but concentrations of approximately 1.8 mg/ml are typical for B-B3, and lower for B-EA6. A wide range of other compounds e.g. pyropheophorbides and various dihydroxychlorins also formulate with ease to give final formulations at 2 mg/ml in 10% P123 in non-optimized systems. Therefore both the drug loading, and stability could be improved further by adjustments to composition, pH, and/or methodology of formulation. Surprisingly, with BPD-MA, greater drug loading was achieved in formulations with P123 than with any other tested poloxamer. This was also borne out with B-ring compounds, which were the most stable in P123 than in any of the other tested poloxamers, under the given conditions.

Preferred poloxamers of the invention include poloxamer 403 (P123), poloxamer 407 (P127), poloxamer 402 (P122), poloxamer 181 (L61), poloxamer 401 (L121), poloxamer 185 (P65), poloxamer 188 (P68), and poloxamer 338 (F108).

In another embodiment it is preferred that the molar ratio of the copolymer to drug be equal to or greater than one. The present invention includes the discovery that increased ratios of copolymer to drug improves drug "loading" into the disclosed medicament and carrier, or medicament and carrier and solid support, formulations.

In one embodiment of the invention, blends of block copolymers with other ionic and non-ionic surfactants, and other materials may be used to supplement, or compensate for physical and chemical properties lacking in the primary copolymer. For instance, the "oiliness" or difficult hydration of a certain copolymers may be counteracted by inclusion of one or more hydrophilic copolymer(s) or other surfactant families such as, but not limited to PEG, PVP, Triton, Tween, or amphiphilic substances such as bile salts and lipids or lipid derivatives. As an illustration of this embodiment, blending Pluronic®F127 and P123 is demonstrated in Example 15 below. This example also illustrates that blending poloxamers of different characteristics improves subsequent hydration and stabilizes the formulation compared to single poloxamer. Thus specific blends of block copolymers are contemplated for use in the invention in combination with medicaments in general, and photosensitizers in particular.

Mixed micelle systems have been shown to be highly effective in drug stabilization (Krishna et al. Journal 52, 6, 331-336, 1998). Micelles composed of hydrophobic drug-hydrophobic copolymer might be stabilized in aqueous suspension upon addition of one or more hydrophilic copolymer(s), or other surfactant families such as, but not limited to PEG, PVP, Triton and Tween. Ionic surfactants could be envisaged to embed themselves into the hydrophobic micelle with the hydratable headgroup providing high charge density at the micelle water interface. A similar effect might be achieved by blending block copolymers with a low molecular weight, highly water-soluble block copolymer or other surfactant material but not limited to bile salts and their derivatives, fatty acid derivatives, amino acids or other charged head groups. In another embodiment of the invention, photosensitizers can be formulated in mixed micelle systems of ionic and non-ionic polymers. Mixed micelles have been shown to effect drug stabilization (Chow & Bernard, J. Pharm Sci, 70, 8, 924-926, 1980, Krishna et al. Journal 52, 6, 331-336, 1998).

In yet another embodiment, photosensitizers can be formulated as simple oil in water (O/W) emulsions or W/O/W emulsions for formulation of photosensitizers using block copolymers. Certain poloxamers e.g., Pluronic® L61, L121, L122 spontaneously form emulsions in the absence of emulsifiers, or other stabilizing additives. Additionally, formulations of L122 can be filtered through 0.2 µm sterilization filters with no loss of drug, and therefore suggesting a very small particle size. These emulsions have been found to be stable over several days (see Table 3 below).

In an additional embodiment, hydrophobic copolymers with and without photosensitizers could be used as an adjunct to PDT, to improve the therapeutic index of the PDT treatment in their capacity as immunoadjuvants, e.g. in the treatment of metastatic lesions, disperse tumors or inflammatory lesions with microbial or autoimmune involvement.

In a further embodiment, the gelling properties of block copolymers can be utilized for preparing ocular formulations. Photosensitizing drugs can be formulated in block copolymer for eye drops for ocular lesions to be treated; for example, hypervascularised areas in macular degeneration, those induced by irritants e.g. excessive exposure to UV. On account of the detergency and surfactant properties, intraocular formulations of photosensitizers in poloxamers (or post PDT washes) would aid in clearing away of cellular debris generated following localized PDT e.g. for glaucoma and other conditions.

Moreover, topical and mucosal copolymer formulated preparations are applicable, but not limited to, mucoadhesive preparations for inflammatory and autoimmune disorders for example, inflammatory bowel disease alopecia, psoriatic lesions.

In another embodiment the surfactant properties of copolymer formulations could be exploited to enhance dermal penetration of photosensitizing drugs, or that of psoriatic and other lesions. Penetration of the blood brain barrier by poloxamers has also been documented and could prove beneficial in the PDT treatment of brain tumors or other disorders. (See Kabanov et al., J. Contr Rel. 22, 141-158, 1998).

In yet another embodiment, cellular uptake of photosensitizers can be accelerated using copolymer formulations. The applicants have shown in Example 11 below that cellular uptake of photosensitizers is accelerated by utilizing poloxamer formulations.

In a further embodiment the copolymer formulations can be used to induce the permeabilization of cellular membranes of the photosensitizers. Cellular internalization of the drug and its intracellular localization is critical in determining the final outcome of PDT. The wetting capacity of copolymers to induce permeabilization of cellular membranes could be exploited using compositions either with or without photosensitizers.

Parenteral administration of block copolymers would be useful in treating all the disorders mentioned above, particularly where treatment or elimination of microvasculature is required. The advantage with poloxamers is that it can be used to formulate highly hydrophobic photosensitizer drugs. Poloxamers have been found to be useful in the invention for formulation of hydrophobic photosensitizer drugs because of their high solubility in both aqueous systems and volatile solvents in which hydrophobic compounds such as BPD-derivatives display good solubility.

In another embodiment administration of block copolymer formulation of photosensitizers could be used for the treatment of various types of cancers. Example 29 illustrates reduction of tumor recurrence in tumor mice model, which were treated with poloxamer photosensitizer formulation. In a further embodiment block copolymers allows both a greater proportion of the medicament to target tissues compared to other formulations. This is illustrated in Example 29 where poloxamer formulations were compared to liposomal formulations using a mice tumor models.

Preferably, solvents used in the invention when medicaments or photosensitizers are not dissolved into a liquefied carrier, include any organic volatile solvent or mixture of solvents that are capable of dissolving the carrier and photosensitizer but not the solid-support. The choice of solvent to use is based in part on the hydrophobicity of photosensitizers and type of carriers, and the choice can be readily made, or made upon routine experimentation, by the skilled artisan. Exemplary solvents used to illustrate this invention include, but are not limited to, methylene dichloride and ethanol.

Deposition or enclosing of the medicament (photosensitizer)-carrier mixture in the presence of a support is by any known process which will not damage the medicament (photosensitizer) or the carrier components in the process. A commonly used means for small-scale preparation is the solvent rotary vapor evaporator. Preferred processes are, but not limited to, air drying, heat drying, spray drying, Wurster type coating technology (Wurster, J. Amer. Pharm. Assoc. 48:451, 1959), lyophilization, and use of compressed or super critical fluid granulation.

The following processes can be used for formulations in the presence, or even the absence, of a solid support. Depending on the state of the medicament-carrier mixture and whether the medicament is labile, there are a number of ways of removing the fluids that may be present in the formulation mixture. Spray-drying techniques can be used for medicament-carrier that is in a liquid (molten or in solution) state. For block copolymers that revert to solid state on cooling, the spray dried product can be further micronized or ground to increase the surface area for hydration. Wurster-type technology can be used for semi-solid block copolymers to envelope or coat using exo-support, like a sugar, to prevent agglomeration of the spray dried particles. Supercritical fluid process is a single step process that can accomplish removal of fluids (solvents) from a mixture and results in granules. The granules produced by this process are generally highly porous and result in rapid hydration. This process can be used for medicament and carrier mixture. Supercritical fluid using $CO_2$ has been used for preparing polymeric microparticles and the advantages over other methods have been discussed byBodmeier et al. (Pharm. Res. 12 (8): 1211-1218,1995). It is highly preferred that supercritical fluids be used for forming granules for both liquid and solid block copolymers.

The solid product from the above processes can be subsequently hydrated or combined with alternative formulations depending on the mode of application or usage for instance, mixing with ointment bases for topical applications.

Hydration of the medicament carrier with or without the support may be accomplished by addition of an aqueous based solution. The choice of aqueous solution may depend on the components of the formulation mixture and how the hydrated complex is to be used. The aqueous based solution may be water or buffer, which may or may not contain various excipients or stabilizers. The hydrated complex can be processed further if required, or lyophilized or otherwise desiccated for storage. The formulation may be prepared under Good Manufacturing Procedures (GMP). If the components are not sterile, the formulation may be sterilized by any known method in the art. These include heat, filter, radiation, and sterilization under conditions suitable for the medicament-carrier mixture.

C. Solid Supports

The supports useful in the invention include both endo- and exo-supports that permit improved hydration in comparison to medicament-carrier formulations prepared without such supports. The role of the support is to maintain the precursor medicament and carrier formulation in a dry state prior to hydration and use. The support is preferably chosen so that it does not dissolve in the carrier or solvent used to dissolve the medicament. Endo-supports are defined as any support that can be used for depositing the medicament and carrier on the surface of the support and that allows for hydration of the medicament and carrier in an aqueous based medium. An exo-support is defined as any support that partially or wholly coats or encloses or encapsulates the medicament and carrier mixture.

In one embodiment the support that is suitable for this invention are those that are non-toxic, biodegradable, not soluble in organic volatile solvents or carriers used for dissolving the medicament (photosensitizer), suitable for deposition or encapsulation of the mixture, and suitable for hydration of the deposited mixture in an aqueous based medium.

It is preferred that the endo- and exo-support are finely divided and porous such that hydration of the deposited mixture is promoted due to increased surface area.

In one embodiment the endo-support material is soluble upon hydration of the deposited medicament (or photosensitizer) and carrier mixture. Preferred endo-support material include, but are not limited to, ionic salts, lactose, dextrose, sucrose, trehalose, sorbitol, mannitol, xylitol or a naturally occurring polymers and amino acids or derivatives thereof. The more preferred material is lactose and the most preferred is trehalose, which may function both as a solid support and a hydration aid for a medicament/canier mixture. These embodiments are illustrated in Examples 16 to 20 below, which show the use of such endo-supports for depositing formulations of photosensitizer and one or blend of block copolymer carriers. For illustration purposes the photosensitizers tested were the A and B-ring tetrapyrroles, the carriers were non-blended and blended block copolymers from the poloxamer group and the endo-support were the hydratable sugars such as lactose or trehalose.

Blended poloxamers with dissolvable solid-supports were found to hydrate faster than blended poloxamers without the solid-support. Examples 17 to 20 below demonstrate the use of blended poloxamers P123 and F127 with hydratable solid-supports lactose or trehalose.

In another embodiment the solid-support can be of material that is insoluble in liquefied carrier, solvent, or aqueous based solution but allows for hydration of the deposited mixture from the surface of the solid-support. In the latter case the solid-support material is preferably non-toxic, biodegradable and/or easily removed from the hydrated formulation. Such materials include any be any polymeric material that has been found to be suitable for therapeutic use or implants.

Examples 22 to 27 below illustrate the use of hydratable solid-supports for liposome-formulated photosensitizers of the A-ring tetrapyrroles compounds.

D. Pharmaceutical Compositions and Administration

The photosensitizer is formulated into a pharmaceutical composition by mixing the medicament (or photosensitizing agent) with one or more physiologically acceptable carriers, i.e., carriers that are non-toxic to recipients at the dosages, concentrations and modes of administrations employed. The medicament may be used in its solid form or dissolved in an appropriate solvent for addition to the carrier (solid or liquefied) or dissolved in an appropriate solvent. Preferred mixtures should be in appropriate solvents for dissolving both medicament and carrier, and at the desired degree of medicament purity. It is preferred that upon hydration, at the appropriate pH for the medica ment, the photosensitizer and carrier fo rm a complex which facilitates delivery of the photosensitizer to the target. Other additives and pharmaceutical excipients can also be added, during or after formulation, to improve the ease of formulation, formulation stability, speed of reconstitution, delivery of the formulation. These include, but are not limited to, penetration enhancers, targeting aids, anti-oxidants, preservatives, buffers, stabilizers, solid support materials. The composition may include osmoregulators if required, such as but not limited to, physiologically buffered saline (PBS), carbohydrate solution such as lactose, trehalose, higher polysaccharides, or other injectable material. A wide variety of excipients and stabilizers are known in the art and their use will depend on the formulation type and application requirements. The function of stabilizers is to provide increased storage stability in cases where the photosensitizer or carriers are labile to heat, cold, light or oxidants or other physical or chemical agents. Other purpose for stabilizer may be for maintaining photosensitizer and/or carrier in a form appropriate for transport to and uptake at the target site. Depending on the solubility, the excipients or stabilizers may be added either prior to deposition step or after the hydration step.

The formulations of the invention may be incorporated into convenient dosage forms, such as capsules, impregnated wafers, ointments, lotions, inhalers, nebulizers, tablets, or injectable preparations. Preferably, the formulations of the invention are administered systemically, e.g., by injection. When used, injection may be by any known route, preferably intravenous, subcutaneous, intradermal, intramuscular, intracranial or intraperitoneal. Injectables can be prepared in conventional forms, either as solutions or suspensions, solid forms suitable for solution or suspension in liquid prior to injection, or as emulsions. Intravenous preparations can be administered as a bolus injection or by controlled infusion following prior dilution if deemed necessary. Controlled intravenous injection is especially preferred following reconstitution, or dilution of the reconstituted drug substance in a physiologically acceptable aqueous preparation. Solid or liquid pharmaceutically acceptable carriers may be employed. Solid carriers include starch, lactose, calcium sulfate dihydrate, terra alba, sucrose, talc, gelatin, agar, pectin, acacia, magnesium stearate and stearic acid. Liquid excipients include syrup, peanut oil, olive oil, saline, water, dextrose, glycerol and the like. Similarly, the carrier or diluent may include any prolonged release material. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Remington's Pharmaceutical Sciences, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral delivery, including topical, transdermal, mucosal, intravaginal, intranasal, intrabronchial, intracranial, intraocular, intra-aural and rectal administration. The pharmaceutical preparations may also contain minor amounts of nontoxic auxiliary substances such as wetting or emulsifying agents, pH buffering agents and so forth. Pharmaceutical compositions formulated for timed release may also be prepared. The preparations may include osmoregulators if required, such as but not limited to, physiologically buffered saline (PBS), carbohydrate solution such as lactose, trehalose, higher polysaccharides, or other injectable material.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable preparations include, but are not limited to, solution, gels, suspensions, emulsions, creams, ointments, powders, liniments, salves, eye drops, and the like. If desired, these may be sterilized or mixed with auxiliary agents, e.g., preservatives, stabilizers, wetting agents, buffers, penetration enhancers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, preservatives, and/or antioxidants in addition to the compounds of the invention.

For the preferred topical applications, especially for humans, it is preferred to administer an effective amount of the formulation to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The formulations of the invention may be given in combination with one or more additional compounds that are used to treat the disease or condition. For treating cancer, the formulations are given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical preparations comprising any known cancer therapeutic in combination with the formulations disclosed herein are within the scope of this invention.

The pharmaceutical preparations of the invention may also comprise one or more other medicaments such as anti-infectives including antibacterial, anti-fungal, anti-parasitic, anti-viral, and anti-coccidial agents.

Typical single dosages of the formulations of this invention are between about 1 ng and about 10 g/kg body weight. The dose is preferably between about 0.01 mg and about 1 g/kg body wt. and, most preferably, between about 0.1 mg and about 100 mg/kg body wt. For topical administration, dosages in the range of about 0.01-20% concentration of the compound, preferably 1-5%, are suggested. A total daily dosage in the range of about 1-500 mg is preferred for oral administration. The foregoing ranges are, however, suggestive, as the number of variables in regard to an individual treatment regime is large, and considerable excursions from these recommended values are expected.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", Canc. Chemother. Reports, Part 3, 3:1-112.

E. Drug Release

In liposomal formulations of BPD-MA, drug fluorescence is concentration quenched due to its location in the liposomal membrane. This allows its release to plasma proteins to be monitored. This is not the case for copolymer formulations which do not display fluorescence quenching, in which case it is assumed that the drug is encompassed in its non-aggregated form in a more dynamic micellar system. It is therefore likely to be released instantaneously in the presence of alternative drug-binding molecules (such as lipoproteins) upon injection into the circulation. Example 11 below shows the high level of association of B-ring drugs with the lipoprotein fraction following a very brief exposure to human plasma.

F. Photodynamic Therapy

Preferably, electromagnetic radiation, such as from ultra-violet to visible and infra red light, is delivered after administration of the compositions and formulations of the invention. Also preferred in the invention is the use of low-dose PDT. By "low-dose PDT", it is meant a total photodynamic therapy experience at substantially lower levels of intensity than that ordinarily employed. Generally, there are three significant variables—the concentration of the photosensitizing drug, the intensity of the radiation employed and the time of exposure to light, which determines the total amount of energy ultimately delivered to the target tissue. Generally, an increase in one of these factors permits a decrease in the others.

For example, if it is desired to irradiate only for a short period of time the energy of irradiation or the concentration of the drug may be increased. Conversely, if longer time periods of irradiation are permitted, lower irradiation intensities and lower drug concentrations are desirable. In some instances, the combination of 0.15 mg BPD-MA as a drug concentration and approximately 1 J/cm2 total radiation from an appropriate radiation source provided successful results. The use of low dose PDT offers an additional advantage in the form of reducing the likelihood of PDT side effects such as damage to unintended tissues.

It is understood that the manipulation of these parameters will vary according to the nature of the tissue being treated and the nature of the photosensitizer (PS) employed. However, in general, low-dose PDT employs combinations of the drug concentration, radiation intensity, and total energy values which are several fold lower than those conventionally used for destroying target tissues such as tumors and unwanted neovascularization. One measure might be the product of PS concentration (e.g., in ng/ml) x intensity (e.g., in mW/cm2)×time (e.g., in seconds). However, it is difficult to set absolute numbers for this product since there are constraints on each of the parameters individually. For example, if the intensity is too low, the PS will not be activated consistently; if the intensity is too high, hyperthermic and other damaging effects may occur. Additionally, in some instances, ambient or environmental light available at the target cell or tissue undergoing PDT may be sufficient in the absence of additional deliberate irradiation.

Similarly, PS concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the PS employed, and in general, an increase in intensity would permit a decrease in time of irradiation, and so forth.

Having now generally described the invention, the same will be more readily understood through reference to the following examples which are provided by way of illustration, and are not intended to be limiting of the present invention, unless specified

EXAMPLES

General Comments

The following general comments on materials apply to the following examples, unless otherwise noted.

BPD-MA, BPD derivative EA6, and B3 A and B ring compounds were synthesized as described in the patents recited above. BPD-MA, A-EA6, B-EA6, A-B3, and B-B3 were obtained from QLT PhotoTherpeutics Inc. (Vancouver, B.C., Canada; QLT).

Example 1

Prescreening of Block Copolymers for Photosensitizer Drug Loading

The following example illustrates the pre-screening of block copolymers for utility in drug loading for intravenous delivery by studying the aqueous suspension characteristics.

Although certain block copolymers have been used previously as emulsion stabilizers in various pharmaceutical formulations, block copolymers which themselves emulsify in aqueous suspension have not been studied in great detail for parenteral formulations. This has been due to the greater difficulty in controlling and maintaining particle size during manufacture and storage. Ideally, a stable micellar suspension is preferred. For extended shelf life, the final formulation is required to be in a dry form which is easily reconstituted for injection. An acceptable minimum reconstituted drug concentration for an intravenous formulation is in the range of 1-2 mg/ml with at least 4h post reconstitution stability in aqueous suspension. Important considerations for intravenous formulation are (i) delivery of drug in a non-aggregated form, (ii) low viscosity preparations (iii) non-frothy preparations, and (iv) sterile filterability prior to lyophilization. A criterion for hydrophobic drug formulation is effective delivery to the plasma lipoproteins, which act as intermediate drug carrier in vivo to tissues displaying high levels of LDL receptors. These include hyperplastic tissues and those undergoing repairs, e.g. under inflammatory conditions.

In this experiment the copolymers were pre-screened for their potential as injectable drug formulation agents, starting with the examination of their aqueous suspension characteristics at various concentrations i.e. whether they formed emulsions or solutions in water. The Pluronic® copolymers used in this and subsequent experiments were obtained from BASF Corp. and are described in the following table with their PPO/PEO contents and molecular weights.

5 ml suspensions of each Pluronic® were made at 5%, 10%, 15% and 20% w/v in physiologically buffered saline (PBS), pH 7.4. This was facilitated by sonicating the suspensions in a water bath (Aquasonic, 250D, VWR Scientific) at 55° C. The suspensions were then examined and the viscosity of each suspension was determined visually by the thickness of film left on vial wall as it was tilted, and by relative ease of filtration through 0.2 [1] m filters (Sterile Acrodisc® 13, Gelman Sciences).

TABLE 1

| Poloxamer[1] | Pluronic ®[2] | PEO[7] (a) | PPO[8] (b) | MW (g/mol) |
|---|---|---|---|---|
| 401 | L[3]121 | 6 | 67 | 4400 |
| 402 | L122 | 13 | 67 | 5000 |
| 403 | P[4]123 | 21 | 67 | 5750 |
| 407 | F[5]127[6] | 98 | 67 | 12000 |
| 338 | F108[6] | 128 | 54 | 15000 |
| 181 | L61 | 3 | 30 | 2000 |
| 185 | P65 | 19 | 30 | 3400 |
| 188 | F68[6] | 75 | 30 | 8350 |
| 124 | L44[6] | 11 | 21 | 2200 |

[1]Block copolymer Poloxamer No.
[2]Pluronic ® No. (BASF) equivalent to [1]Poloxamer No
[3, 4, 5]Pluronic No. prefix: L[3]: liquid; P[4]: paste; F[5]: flake
[6]Available in NF grade (from BASF)
[7]PEO: poly(ethylene oxide)
[8]PPO: poly(propylene oxide)

Table 2 summarizes the qualitative results of the solution appearance, viscosity and filterability of 5 to 20% weight by volume (w/v) concentration range of the different types of poloxamers in PBS. Generally, viscosity in both solutions and emulsions increased with Pluronic concentration. Copolymers forming highly viscous suspensions (e.g. preparations at higher Pluronic concentrations) or those forming highly unstable emulsions e.g. L61 were not further tested. Copolymers with a lower PEO content less that 30% (L61, L121, L122) displayed limited water solubility, and tended to form oily emulsions rather than clear solutions. Under the above conditions, Copolymers that formed solutions were those with a higher PEO content such as P123, P127, F68, F108, and were tested further for drug loading at lower concentrations.

TABLE 2

Solubility, viscosity and filterability characteristics of poloxamers

| | 5% w/v | | 10% w/v | | 15% w/v | | 20% w/v | |
|---|---|---|---|---|---|---|---|---|
| Pluronic | Appearance/ Viscosity | Filtered | Appearance/ Viscosity | Filtered | Appearance/ Viscosity | Filtered | Appearance/ Viscosity | Filtered |
| L121 | Opaque emulsion | Yes | Opaque emulsion | Yes | Opaque emulsion | Yes | Gels | No |
| L122 | Frothy emulsion | Yes | Frothy emulsion | Yes | Viscous frothy emulsion | Yes | Gels | No |
| P123 | Clear frothy solution | Yes | Clear frothy solution/ slight viscosity | Yes | Clear frothy solution/ medium viscous | No | Clear frothy solution/ medium viscous | No |

TABLE 2-continued

Solubility, viscosity and filterability characteristics of poloxamers

| Pluronic | 5% w/v Appearance/Viscosity | Filtered | 10% w/v Appearance/Viscosity | Filtered | 15% w/v Appearance/Viscosity | Filtered | 20% w/v Appearance/Viscosity | Filtered |
|---|---|---|---|---|---|---|---|---|
| F127 | Clear solution/low viscosity | Yes | Clear solution/medium viscosity | Yes | Clear solution/high viscosity | Yes | Clear solution/high viscosity | No |
| L61 | Oily emulsion/low viscosity | No | Oily emulsion/low viscosity | No | Oily emulsion/low viscosity | No | Unstable emulsion | No |
| P65 | Frothy solution/low viscosity | Yes | Frothy solution/low viscosity | Yes | frothy solution/low viscosity | Yes | frothy solution/low viscosity | Yes |
| F68 | Clear solution | Yes | Clear solution | Yes | Clear solution | Yes | Slightly viscous | Yes |
| F108 | Clear solution | Yes | Frothy viscous solution | Yes | High viscosity solution | No | High viscosity solution | No |

Example 2

Photosensitizer Drug Loading of BPD-MA using PEO-PPO-PEO Block Copolymers

The following example illustrates the utility of block copolymers for drug loading of an A-ring tetrapyrrolic compound.

In this experiment the use of copolymers for drug loading capability and formulation stability over a 3 day period was examined using the photosensitizer drug BPD-MA. The criteria for choosing the copolymers were based on the solution and viscosity characteristics described in Example 1. The 'melt' method is used for the preparation and screening of the large number of samples and is described as follows. At temperatures above 50° C., poloxamers are in their molten state and serve as excellent solvents for tetrapyrrolic compounds, thus avoiding the need for pre-dissolution of drugs in organic solvents. 5 mg of BPD-MA was dissolved with the aid of vortex mixing and sonication at 55° C. into the polymer 'melts' to give a final concentration of 5% to 20% w/v of the respective Pluronic. To each melt sample, 2.5 ml of PBS was added to give a final BPD-MA concentration of 2 mg/ml. Samples were allowed to equilibrate to room temperature before drug loading was determined at time zero ($T_0$). 1 ml of suspension was removed for centrifugation (Microfuge, 14,000 rpm, 30 min), and the rest filtered through 0.2 µm filters (Millipore). The filtrate was diluted 1:100 in PBS and the absorbance at 690±3 nm determined (uv-vis spectrophotometer Beckman DU-6401). This procedure was repeated 72 hours later following storage at room temperature and the absorbance measurement ($T_{72}$).

The following table summarizes the results of the above experiment.

TABLE 3

Absorbance ($A_{693}$) of BPD-MA of filtered (F) and centrifuged (C) samples after hydration.

| Pluronic | C/F[1] | 5% w/v $T_0$ | 5% w/v $T_{72}$ | 10% w/v $T_0$ | 10% w/v $T_{72}$ | 15% w/v $T_0$ | 15% w/v $T_{72}$ | 20% w/v $T_0$ | 20% w/v $T_{72}$ |
|---|---|---|---|---|---|---|---|---|---|
| L122 | C | 0.51 | 0.64 | 0.74 | 0.76 | 0.8 | 0.41 | N/D[2] | N/D |
|  | F | 0.61 | 0.53 | 0.76 | 0.73 | 0.43 | 0.57 | N/D | N/D |
| P123 | C | 0.44 | 0.62 | 0.86 | 0.66 | N/D | N/D | N/D | N/D |
|  | F | 0.64 | 0.66 | 0.69 | 0.58 | N/D | N/D | N/D | N/D |
| F127 | C | 0.74 | 0.64 | 0.67 | 0.67 | 0.81 | 0.88 | N/D | N/D |
|  | F | 0.62 | 0.63 | 0.66 | 0.64 | 0.87 | 0.83 | N/D | N/D |
| P65 | C | 0.1 | 0.02 | 0.43 | 0.36 | 0.9 | 0.73 | 1.0 | 0.97 |
|  | F | 0.02 | 0.09 | 0.35 | 0.43 | 0.81 | 0.78 | 0.97 | 0.97 |
| F68 | C | 0.3 | 0.25 | 0.13 | 0.05 | 0.09 | 0.06 | 0.3 | 0.07 |
|  | F | 0.25 | 0.33 | 0.06 | 0.13 | 0.11 | 0.07 | —?? | 0.24 |
| F108 | C | 0.17 | 0.19 | 0.72 | 0.65 | N/D | N/D | N/D | N/D |
|  | F | 0.59 | 0.58 | 0.68 | 0.73 | N/D | N/D | N/D | N/D |

[1]N/D — Not done

The results show that highest drug loading using 5% w/v copolymers gave A693 ranging from 0.5 to 0.7 for L122, P123 and F127 in both centrifuged and filtered preparations. These copolymers have the highest PPO content (67 Units). Drug loading using 10% w/v copolymer showed highest drug loading with L122, P123 and F127 and F108 (PPO 54 units) with $A_{693}$ ranging from 0.58 to 0.76. P65 (PPO 30 units, PEO 19 units) showed minimal incorporation at 5 and 10% w/v but total incorporation at 15 and 20% w/v. Drug loading was greater than in F68 that has the same number of PPO units. Solution forming poloxamers such as P123, L122 and F127, show little discrepancy between centrifuged and filtered samples, suggesting that both procedures were equally effective in removing unincorporated photosensitizer drug aggregates from the formulations. The $A_{690}$ reading were comparable between day 0 and day 3 which implied that there was no loss of stability of BPD-MA formulations in Pluronic following 3 days storage.

Based on the observation that greater drug loading is dependent on lower water solubility (low PEO) within a given PPO group, but without being bound by theory, it seems possible that micelle formation is important for stabilization of highly hydrophobic drug substances. A reason why F68 does not perform well may be because of its high water solubility. The extended PEO chains (PEO 75 units) would not be conducive to micelle formation.

Example 3

Photosensitizer Drug Loading of B-B3 Using Pluronic Block Copolymers

The following example illustrates the utility of block copolymers for drug loading of B-ring tetrapyrrolic compounds, and maintaining the drug in a non-aggregated form.

For this experiment copolymers were examined for drug loading capability and formulation stability over a 24 h period using the drug B-B3. The experimental procedure is the same as described in Example 2 with the following exceptions. The copolymers were tested at 10%, 15% and 20% w/v. For convenience centrifugation rather than filtration was used to eliminate unincorporated drug prior to absorbance measurement. It has previously been observed that aggregates of B-ring compounds have a characteristic red shifted, high extinction absorbance at 730 nm±10 nm, which takes place at the expense of the typical 690 nm absorbance attributed to monomers. The 730 peak correlates with sub-optimal formulation conditions, and has proved useful for evaluation of formulation quality. Dissolution of green crystalline B-ring compounds in melted poloxamers resulted in a reddish brown solution absorbing entirely at 690 nm. Similar color was observed in stable formulations of B-ring compounds in aqueous suspensions of poloxamers.

Table 4 shows results of B-B3 drug loading using various block copolymers. Overall, the results for B3-B drug loading displayed the same general pattern as for BPD-MA as seen in Example 2, but with lower drug loading. Polymers L122, P123 and F127 showed the highest drug loading. Unlike loading of BPD-MA in P65 (Example 2), the drug loading was comparable to the PPO 67 unit group, this was not the case for B-B3, even at the highest P65 concentrations tested.

TABLE 4

Absorbance ($A_{693nm}$) of B-B3 formulation following hydration and centrifugation

| Pluronic ® | 10% w/v | | 15% w/v | | 20% w/v | |
|---|---|---|---|---|---|---|
| | $T_0$ | $T_{24}$ | $T_0$ | $T_{24}$ | $T_0$ | $T_{24}$ |
| L122 | 0.54 | 0.50 | 0.5 | 0.56 | N/D | N/D |
| P123 | 0.52 | 0.53 | N/D | N/D | N/D | N/D |
| F127 | 0.57 | 0.4 | 0.51 | 0.48 | N/D | N/D |
| F108 | 0.1 | 0.015 | N/D | N/D | N/D | N/D |
| P65 | 0.07 | 0.07 | 0.15 | 0.13 | 0.36 | 0.24 |
| F68 | 0.03 | 0.025 | 0.02 | 0.02 | 0.03 | 0.03 |

(n = 2)

On 1:100 dilution, the P123 formulation displays a 690 nm absorbance in PBS which is similar to that in organic solvents e.g. methanol suggesting a similarly hydrophobic environment for the drug in the Pluronic formulation. Twenty minutes following dilution produced a 730 mn peak in the F127 formulation (results not shown), but not in the 10% w/v P123 or L122 formulations. This is again indicative of a micellar organization for the poloxamers in aqueous suspensions, particularly in those with an intermediate PEO content >10% w/w. Highly water soluble polymers such as F127, form unstable preparations particularly on dilution, as the ratio F127:drug decreases resulting in micelle destabilization with consequent drug aggregation.

Centrifugation of unstable formulations (P65, F68, F108) resulted in an aggregated drug pellet absorbing predominantly at 730 nm wavelength, even on suspension in 100% fetal bovine serum. This confirms that the 730 nm peak may indicate low non-aggregated drug bioavailability to plasma lipoproteins and therefore should be avoided in formulation of B-ring compounds.

Example 4

Drug loading of B-EA6 and B-B3 Using Block Copolymers and Thin Film Approach

The following example describes an alternative method for B-ring hydrophobic drugs (B-B3 and B-EA6) that were previously described as being difficult to formulate, and to do so using smaller quantities of drug and block copolymers. Although the melt method described in Example 2 works well for formulating hydrophobic drugs, it requires constant stirring and vortex mixing to maintain the drug in contact with the small volume of block copolymers used. The smallest volume that could be prepared using such a method was approximately 5 ml. Creating a thin film from a solution of both the drug and Pluronic in a volatile organic solvent on the other hand, allows a larger surface area for faster hydration.

The B-ring drugs B-EA6 and B-B3 were tested by the following formulation method. 5 mg of the drug and 0.5 g Pluronic were dissolved in methylene chloride ($CH_2Cl_2$) and combined to give final volume of 2.5 ml in a round bottom flask. The solvent was removed by rotary evaporation, and the resultant thin film hydrated with 2.5 ml PBS at 50° C. in a sonication bath. After cooling to room temperature (1-2 hours), samples were centrifuged to remove unincorporated drug, and A690 of 1:100 dilutions was determined.

The results of formulating B-B3 and B-EA6 by the poloxamer based thin film approach are summarized in Table 5.

TABLE 5

| | Absorbance($A_{690}$) | |
|---|---|---|
| Pluronic (10%) | B-B3 | B-EA6 |
| P123 | 0.8 | 0.315 |
| L122 | 0.6 | 0.275 |
| F127 | 0.4 | 0.08 |

It was surprising to note that B-EA6 could be formulated with block copolymers because of earlier poor results obtained with other carriers and liposomal formulation attempts. B-B3 was more readily formulated in poloxamers compared to B-EA6 under the above conditions. The order of formulation efficiency remained the same as observed in Example 3, i.e. F123>L122>F127. Both drug preparations in 10% F127 developed the 730 absorbance peak within 15 min of dilution in PBS. This was indicative of formulation destabilization and drug aggregation in aqueous suspensions, perhaps due to an unstable micellar structure.

Example 5

Hydrophobic Photosensitizer Drug loading Using Block Copolymers

The following example illustrates one embodiment for hydrophobic drug loading using block copolymers.

Unless otherwise stated, the following protocol was used for all subsequent formulation of the photosensitizer drugs in poloxamers:

1 to 2 mg drug and 25-100 mg Pluronic are combined in methylene dichloride ($CH_2Cl_2$) to yield drug concentration of 1 mg/ml. $CH_2Cl_2$ is removed rapidly by rotary evaporation (Rotavapor R-124, Bucchi B172 Vacobox pump) at 50°, at maximum speed of rotation. Once a steady minimum pressure is achieved, the flask is held under vacuum for a further 20-30 min. The resulting thin film is hydrated with 1 ml of physiologically buffered saline (PBS, pH 7.4) or 9.5% w/v lactose, using hand swirling (with glass beads) at 23° C., to give a final drug concentration of 1 or 2 mg/ml, 2.5-10% (w/v) Pluronic as required. Samples are kept overnight at room temperature to allow unincorporated drug to fall out, and then spun at 14,000 rpm {Eppendorff, Microfuge} for 30 min. Supernatant is decanted off into a fresh Eppendorff vial, and diluted 1:100 in the iso-osmolar medium used for thin film hydration (PBS or lactose) for determination of absorbance 690 nm ($A_{690}$). Formulations are stored at 4° C. or frozen at –20° C. for long term storage.

Example 6

Protocol for Liposomal Photosensitizer Drug Formulation

The following example describes a protocol for liposomal preparation of hydrophobic photosensitizers. It is based on existing methodology (Hope et al., Biochim. Biophys. Acta 812, 55-65, 1985).

5 mg drug and lipids (40% EPG in DMPC) are combined in $CH_2Cl_2$ at a drug to lipid ratio of 1:10 w/w in 250 ml round bottom flask. The maximum concentration of drug in solvent is 2 mg/ml. $CH_2Cl_2$ is removed rapidly as described in Example 5. The resulting thin film is hydrated with 2.5 ml lactose solution (9.5% w/v) using hand swirling with glass beads at 40° C. Extrusion using Model 4T (Lipex Biomembranes Inc. B.C., Canada) is carried out with the thermostat set at 40° C. The multilamellar vesicles (MLVs) arising from hydration steps of the liposomal formulation were also examined under the microscope. MLVs are successively extruded 5 times through each of the 400 nm, 200 nm and 100 nm polycarbonate membranes (Nuclepore PC, Costar). Extruded samples were diluted 1:100 in PBS (pH 7.4) and the absorbance determined at 690 nm wavelength.

Example 7

Comparison of Liposomal and Block Copolymer Photosensitizer Formulations

This example demonstrates that micellar formulations of photosensitizers using block copolymers were either comparable or superior to the liposomal formulations.

In this experiment liposomal and block copolymer (micellar) photosensitizer formulations of A- and B-ring compounds of EA6 and B3 were compared. Each of the photosensitizer samples was prepared at a final drug concentration of 2 mg/ml. The block copolymer P123, and the liposomal formulations were prepared as described in the Examples 5 and 6, respectively.

Table 6 shows the results of the photosensitizer drug loading using 10% P123 and liposomes. The A-rings could be formulated using liposomes but formulation of the B-ring compounds was not very efficient. P123 was found not only able to formulate the A-ring compounds but also the B-ring compounds. With the exception of A-B3, the overall results for the drug loading showed that the P123 formulations were either superior or comparable to the liposomal formulation.

TABLE 6

| Drug | Liposome mg/ml | P123[1] mg/ml |
|---|---|---|
| A-EA6 | 0.98 | 1.82 |
| A-B3 | 1.84 | 1.33 |
| B-EA | 0.06 | 0.37 |
| B-B3 | Very low | 1.24 |

[1]Pluronic P123 10% weight/volume

It was observed that in the liposomal formulation the step of hydration of thin film of the A-ring compounds took place readily with the total drug incorporation into MLVs. Microscopic examination did not reveal presence of aggregates. Extrusion took place readily under low pressure without significant loss of drug. In contrast, MLVs arising from hydration of B-ring films were unevenly shaped, with drug aggregates and crystalline structures commonly present. These crystals were problematic because they caused filter blockage during the extrusion process and resulted in significant drug loss. Liposomal formulation with B-ring preparations resulted in very small quantity being incorporated in the liposomes (Table 7).

Formulation with block copolymer P123 resulted in ready hydration of thin films of the A-ring compounds. For the B-ring compounds there was greater drug incorporation using P123 compared to the liposomal formulation.

The above example demonstrates that block copolymer P123 readily incorporated different types of photosensitizers with either similar or superior drug loading compared to the liposomal formulations.

Example 8

Formulation of Dihydroxychlorins in Block Copolpymers

The following example illustrates the use of block copolymer for formulating dihydroxychlorin photosensitizers.

In this experiment the following three selected dihydroxychlorins were examined for formulation with 10% P123. Each of the drugs was prepared to a final concentration level of 1 mg/ml and the formulation protocol used is described in Example 5. These compounds were prepared as described in U.S. patent application Ser. Nos. 09/551,159 and 09/551,160, both filed Apr. 14, 2000, and No. 60/129,324, filed Apr. 14, 1999, all three of which are hereby incorporated by reference as if fully set forth. One of these compounds, JM4, was further tested for drug incorporation using 2.5 to 10% P123.

TABLE 7

| ID No. | Formula |
|---|---|
| JM3 | T(m-OH)PC = 5, 10, 15, 20-tetra (meta-hydroxyphenyl)-2-3-dihydroxychlorin |
| JM 4 | T (p-Me) PC = 5, 10, 15, 20-tetra (para-methyl phenyl)-2,-3-dihydroxychlorin |
| JM 24 | $H_2DPC(OH)_2$ |

All of the above dihydroxychlorin compounds were formulated with ease using 10% P123. The compounds underwent total incorporation with no pellet formation on centrifugation either directly following formulation or 24h later. The micelle size ranged from 15 to 20 nm measured by laser light scattering (Submicron Particle Sizer Model 370, NICOMP, Santa Barbara, Calif.). The formulation was also found to be stable following overnight storage.

Table 8 shows the results of drug incorporation using different concentration of the copolymer P123. The readings following overnight storage and centrifugation. Formulation of JM4 at 2 mg/ml showed that the amount of drug incorporated was found to be dependent on the concentration of polymer in the formulation.

TABLE 8

| P123 % w/v | Incorporation mg/ml |
|---|---|
| 2.5 | 0.92 |
| 5 | 1.43 |
| 10 | 2.00 |

The above example demonstrates the versatility of the P123 block copolymer for formulating different types of photosensitizers. Additionally this example shows that the concentration of the block copolymer will dictate the level of photosensitizer incorporation.

Example 9

Plasma Distribution of Photosensitizers Delivered by Block Copolymer And Liposomal Formulations This example illustrates that B-ring photosensitizers formulated with the block copolymer L123 are delivered with the same or greater efficiency to the lipoprotein fraction of the plasma compared to the standard liposomal formulation of an A-ring compound, BPD-MA.

In this experiment liposomal, block copolymer and dimethyl sulfoxide (DMSO) formulations of the B-ring compounds, B-EA6 and B-B3 were examined for their partitioning between the different components of human plasma. BPD-MA liposomal formulation was used as the standard and the DMSO as a control. Pluronic micellar and liposomal formulations of the photosensitizers were prepared as described in Examples 5 and 6, respectively. DMSO formulation was prepared by direct dissolution of the drug in DMSO.

The assay for centrifugal separation of plasma components was based on Rudel *Biochem J.*, 139, 89-95, 1974.) and subsequently modified by Alison et el. *Photochem. Photobiol.* 52(3): 501-507, 1990). It has been scaled down to allow a shorter centrifugation time. Evidence of clear separation and identities of the different layers has been established. MACE (monoaspartyl chlorin e6) is a relatively water soluble photosensitizer known to be bound and transported by albumin in the circulation. The validity of this assay was further tested using MACE, which was found to be overwhelmingly associated with the albumin (87%), with very little in the lipoprotein layer (11%).

Fresh human plasma was collected in EDTA, and KBr added to give a concentration of 1.21-1.23 g/ml. Photosensitizer formulations were added to 0.8 ml pre-warmed plasma (37° C.) to give a final concentration of 10 µg/ml. 30 sec later, plasma was cooled for 15 min on ice, and under layered with 2.45 ml KBr/EDTA at 1.21 g/ml in thick polycarbonate tubes. Samples were centrifuged at 512K g (100,000 RPM, Beckman TLA 100.3 rotor) for 16-18 h at 20° C. Layer positions were marked to allow determination of layer volume. Each layer was sampled by removing a portion using a syringe inserted from the top. Known volumes of plasma layers were removed into TX/PBS in an 1.8 ml tube (Eppendorf Scientific, Inc., Eppendorf) to give a final concentration of 1% TX. Samples were vortex mixed and then spun for 2 min at 14 000 RPM in an Eppendorf centrifuge for clarification. Fluorescence at 690 nm ($\lambda_{ex}$=434 nm) was read alongside standards of known drug concentration. Total drug present in each layer was calculated on the basis of known layer volume and absorbance value.

Tables 9 and 10 show the percentage distribution of B-B3 and B-EA6, in the various components of the fractionated plasma in comparison to BPD-MA, using liposomal, copolymer and DMSO formulations.

As expected from previous studied liposomal BPD-MA associated predominantly with the lipoproteins (Tables 9 and 10). Comparable results were obtained for the liposomal B-EA6 formulation (Table 9) but not for liposomal B-B3 (Table 10). Surprisingly, the copolymer formulation of B-B3 was found to be superior for delivering the B-B3 to the lipoprotein fraction compared to the liposomal formulation (Table 9). Delivery of the B-EA6 was comparable to the liposomal formulation. The results also showed that delivery of both liposomal and copolymer formulation of EA6-B and B3-B to the lipoprotein fraction was more efficient than with DMSO formulations.

TABLE 9

Percent B-B3 associated with various plasma fractions following centrifugal separation

| Band | Plasma Component | Liposomal BPD-MA % (n = 4) | Liposomal B-B3 % (n = 2) | P123 B-B3 % (n = 6) | DMSO B-B3 % (n = 2) |
|---|---|---|---|---|---|
| A | Lipoprotein | 85.0 (3.6)[1] | 61.4 (1.76) | 91.8 (1.2) | 61.2 (1.12) |
| B' | Salt water | 5.8 (1.4) | 9.4 (0.42) | 4.6 (1.3) | 15.0 (0.21) |
| C' | Albumin | 6.5 (2.3) | 23 (1.51) | 0.8 (0.1) | 1.9 (0.65) |
| C | Other proteins | 0.6 (0.2) | 1.4 (0.01) | 0.4 (0.2) | 4.6 (0.23) |
| X | Pellet | 2.1 (0.8) | 4.8 (0.16) | 2.4 (0.2) | 17.4 (0.47) |
|  | Average Recovery | 79.75 | 95.55 | 103.03 | 76.1 |

[1]value in parenthesis is standard deviation

TABLE 10

Percent B-EA6 associated with various plasma fractions following centrifugal separation

| Band | Plasma Component | Liposomal BPD-MA % (n = 4) | Liposomal B-EA6 % (n = 2) | P123 B-EA6 % (n = 6) | DMSO B-EA6 % (n = 2) | DMSO BPD-MA % (n = 2) |
|---|---|---|---|---|---|---|
| A | Lipoprotein | 85.1 (2.8)[1] | 89.4 (0.04) | 91.4 (2.3) | 59.0 (1.44) | 74.0 (2.3) |
| B' | Salt water | 6.8 (1.0) | 8.5 (0.04) | 3.5 (1.3) | 14.6 (1.10) | 15.7 (1.8) |
| C' | Albumin | 6.9 (1.7) | 0.8 (0.10) | 1.5 (0.6) | 2.8 (0.04) | 6.0 (0.3) |
| C | Other proteins | 0.5 (0.2) | 0.4 (0.01) | 0.2 (0.2) | 2.6 (0.09) | 2.8 (0.4) |
| X | Pellet | 0.7 (0.4) | 0.9 (0.01) | 4.2 (1.8) | 21.0 (2.45) | 1.4 (0.5) |
|  | Average Recovery | 92.05 | 90.8 | 87.17 | 77.95 | 84.2 |

[1]value in parenthesis is standard deviation

Addition of BPD-MA/DMSO to plasma resulted in inefficient delivery to the lipoprotein fraction in comparison to the liposomal formulation. All drugs added to plasma in DMSO resulted in high drug concentration in the salt/water fraction and in the pellet. Although there appears to be a genuine binding to the sedimented flocculent, drug aggregates also end up in the pellet. Low total drug recoveries were observed in DMSO formulations, which probably reflects inadequate dissociation of these aggregates in the detergent system used to read assays.

The above example demonstrates that the copolymer formulations of B-ring compounds are either comparable or superior to the liposomal formulations for the delivery of the drug to the lipoprotein fraction of the plasma. This is important for PDT because most target tissues, those undergoing rapid proliferation or repair, express high levels of LDL receptors, and lipoprotein mediated delivery results in selective accumulation of photosensitizers in these tissues.

Example 10

Cellular Uptake of Liposomal and Polymer Delivery of Photosensitizers

The following example illustrates the efficiency of cellular uptake using block copolymer formulation of a B-ring photosensitizer, B-B3, in comparison with the standard liposomal formulation of BPD-MA.

For this experiment the B-B3 copolymeric formulation and the BPD-MA liposomal formulation were prepared as described in Examples 5 and 6, respectively. The protocol for setting up the cell cultures and conditions for the cellular assay essentially followed Richter et al. (*Proc. SPIE*, 2078: 293-304, September 1993). L1210 cells in DMEM and 10% FBS (single experiment, 3 sets) were incubated with the formulations at a concentration of 3 µg/ml and examined for uptake in the cells over time. Cells were recovered by centrifugation, the pellet briefly rinsed, and the cells lysed by freeze thawing in the presence of 2% Triton X-100®. An equal volume of methanol was added and fluorescence was read at 694 nm ($\lambda_{ex}$ 440 nm).

FIG. 1 shows that cellular uptake of the B-B3 copolymer formulation was very rapid compared to BPD-MA liposomal formulation. 50% uptake level was observed to be close to 'zero' incubation time, with uptake of B-B3 peaking at around 20 min. In comparison, BPD-MA achieved saturation level at 30 min, with 50% uptake at approximately 5 min. It appears that the permeability of cellular membranes to B-B3 is higher in the presence of P123. This is important for the effective penetration of the photosensitizer into the PDT sensitive sites in the intracellular infra structure.

These results suggests that light exposure for PDT treatment in general could be applied as early as 10 to 15 min post injection if the photosensitizer is formulated in copolymers.

The above example demonstrates rapid uptake of a B-Ring photosensitizer by cells when using copolymer. Further because of the rapidity of the photosensitizer uptake using copolymer formulation by the targeted cells, the irradiation step for PDT can be carried out earlier than previously reported for liposomal or other formulations.

Example 11

Comparison of Block Copolymer and Liposomal Photosensitizer Formulations: in vitro Phototoxicity The following example illustrates the advantages of using Pluronic based formulations for effective delivery of B-ring photosensitizer drugs to the cells in a model system.

In this experiment copolymer P123, liposomal and DMSO formulations of the B-ring compounds, B-EA6 and B-B3, were examined for their in vitro cytotoxicity effects. Exposure to drugs was carried out in the presence and absence of fetal calf serum (FCS) as a model to study transfer of drug to cells in vivo. BPD-MA liposomal formulation was used as the standard and the DMSO formulation as the control. The DMSO, Pluronic micellar and liposomal formulations of the photosensitizers were prepared as described in Example 9. A suspension of L1210 cells was prepared and exposed to various drug formulations (drug concentrations ranging from 0-50 ng/ml) either in the absence or presence of 10% fetal calf serum (FCS). One hour later, the drug was removed by pelleting the cells by centrifugation. The pellet was briefly washed with 1 ml DME and resuspended in 5% FCS/DME. 100 µl of the cell suspension was aliquoted into 6 wells of a 96 well plate, and the plate exposed to light at 10 J/cm². Viability was determined 24 h post exposure using the MTT assay (Mosmann, *J. Immunol. Meth.* 65:55-63, 1983).

TABLE 11

| Photosensitizer | Carrier | LD$_{50}$ (ng/ml) −FCS | LD$_{50}$ (ng/ml) +FCS |
|---|---|---|---|
| BPD-MA | Liposomal | 4.0 | 38.0 |
| B-B3 | Copolymer | 0.68* | 16.6* |
| B-B3 | Liposomal | 3.0 | 30.0 |
| B-B3 | DMSO | 7.2 | 37.0 |
| B-EA6 | Copolymer | 2.06* | 12.9* |

TABLE 11-continued

| Photosensitizer | Carrier | LD$_{50}$ (ng/ml) | |
| --- | --- | --- | --- |
| | | −FCS | +FCS |
| B-EA6 | Liposomal | 4.7 | 19.7 |
| B-EA6 | DMSO | 4.7 | 20.0 |

Table 11 shows the LD$_{50}$ values determined for in vitro photocytotoxicity for formulations of B-ring drugs in block copolymers compared to drug delivery using liposomes and solutions in DMSO.

The presence of FCS better represents in vivo conditions for cellular exposure to systemic drugs, and under these conditions it generally competes with the cells for drug binding. However, under both conditions, it is clear from the LD$_{50}$ values that formulations of B-ring drugs in Pluronic have greater potency than liposomal formulations or solutions in DMSO. This indicates superior delivery of drug in a non-aggregated form to cells or plasma proteins. Without being bound by theory, the advantage could also be partly attributed to permeabilization of cellular membranes by poloxamers, which would allow better access of the drug to PDT-sensitive intracellular sites.

The above example demonstrates that the B-ring compounds formulated with P123 were successfully delivered to the cells in a non-aggregated form. The delivery of the photosensitizer drug with the copolymer formulation was found to be superior to the liposomal formulations.

Example 12

Comparison of B-B3 Copolymer and Liposomal Formulations for PDT Treatment of Arthritis in MRL/1pr Mouse Model Arthritis in the MRL/1pr mouse strain was enhanced by giving 2 intradermal injections (thoracic and inguinal sites) with 0.05 ml of complete Freunds adjuvant containing 10 mg/ml heat-inactivated M. tuberculosis. PDT was given on days 0, 10 and 20 following CFA treatment. PDT was carried out as follows; 3 groups of MRL/1pr mice were injected intravenously with B-B3 at 0.5 mg/kg (copolymer or liposomal formulations), after which they were protected from light. The third group was injected with copolymer alone at an equivalent copolymer concentration to that found in the formulation. An hour later, they were exposed to light at 80 J/cm$^2$ for 1.5 h (8 mW/cm$^2$).

Figure 2:
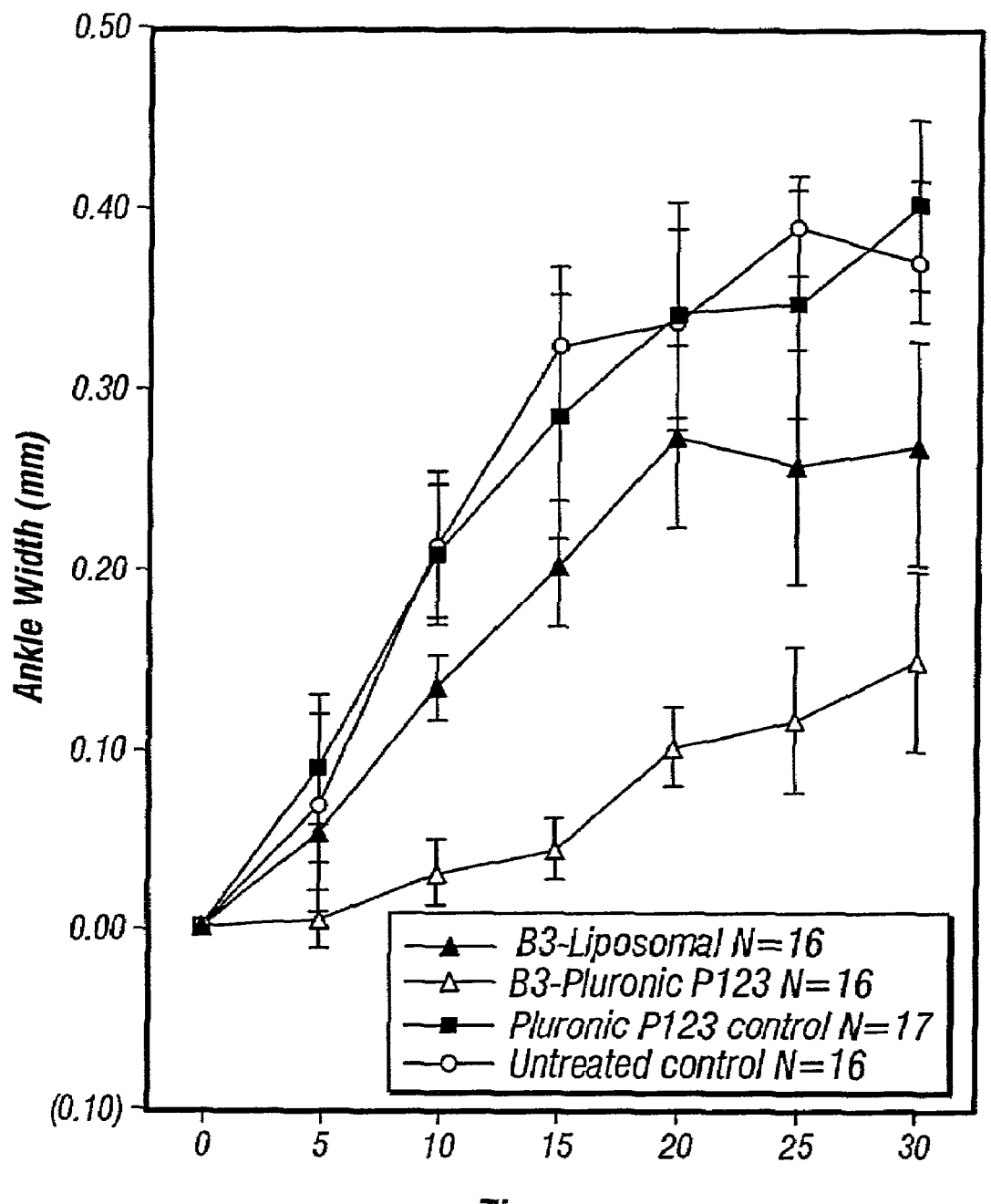
FIG. 2 compares the effectiveness of liposomal and copolymer formulations of B-B3 in controlling joint inflammation in the MRL-lpr mouse model using transcutaneous PDT. Mice receiving copolymer alone exhibited arthritic symptoms similar to the untreated control. The liposomal formulation of photosensitizer B-B3 showed better suppression of the inflammation compared to the controls in the earlier stages. Relative to the controls and the liposomal formulation, the B-B3 copolymer formulation was highly effective in controlling the inflammation as determined by the increase in ankle swelling.

Ankle width measurements were taken every 5 days prior to PDT treatment. The results of the above experiment are shown in FIG. 2. Mice receiving copolymer alone exhibited symptoms similar to the untreated control. The liposomal formulation of B-B3 in earlier part of the study showed better suppression of the inflammation compared to the controls. However, after day 25 there was an exacerbation of the inflammatory condition. Relative to the controls and the liposomal formulation, the B-B3 copolymer formulation was highly effective in controlling the inflammation as determined by increase in ankle swelling.

The above example demonstrates that copolymer formulation of B-B3 is superior to the liposomal formula for controlling an inflammatory disease in vivo in arthritic mouse model.

Example 13

Optimization of B-B3 Intravenous Formulation in Pluronic P123

The following example illustrates the effects of copolymer:drug ratio in achieving total drug incorporation.

Using formulation methods described in Example 5, the aim was to incorporate 2 mg/ml of B-B3 into 10% w/v P123. It was shown by this method that the B-B3 can typically be incorporated at ~1.8 mg/ml drug (based on absorbance readings and a molar extinction coefficient of 30425) 24 h post-hydration. This translates to approximately 10% drug loss. Unincorporated drug undergoes aggregation in aqueous solutions, and is characterized by the appearance of a 730 nm absorbance peak. Although the formulations can be made completely aggregate free by centrifugation or sterile filtration through 0.2 µm filters, this adds another step in the manufacturing process, which can be avoided by increasing the copolymer:drug ratio. A final drug concentration of 1 mg/ml resulted in complete incorporation of all added drug.

Example 14

Blending of Copolymers for Intravenous Formulations of B-B3

To achieve a solid final product, the hydrated material is lyophilized. Alternative means of drying include, but is not limited to, spray or freeze drying. It is important to determine whether the drying process affects the product integrity and to ascertain that formulation characteristics are retained on reconstitution.

In this experiment a 10% P123 (w/v) resulted in a thin film, with an oily appearance, which was difficult to hydrate. Counteracting the oily nature of P123 could be achieved by incorporation of copolymer that is in solid form at room temperature. The use of 1% w/w F127 with 9% w/v P123 instead of 10% P123 (w/v) produced a thin film, which was more readily hydrated. This composition was equally stable and was readily reconstituted following lyophilization. The use of blends may be used to tailor a formulation according to the needs of the particular drug substance and/or to compensate for properties lacking in a primary copolymer. pH studies showed that acidification of B-B3 formulations was detrimental to formulation stability. This necessitates hydration of the solid drug-polymer with a very mild buffer to counteract acidification which occurs upon use of sterile packed distilled water as commonly practiced in clinical settings. Behavior of poloxamers is unaffected by pH, and the use of buffers would be entirely dependent on ionizable groups present on the drug substance. For example, B-EA6 does not display any pH-dependency.

The above example demonstrates that using blend of copolymers for formulating photosensitizer improved the rehydration of the photosensitizer after lyophilization. It also shows that only mild buffers are needed since the copolymer is unaffected by pH, unlike liposomes.

Example 15

Deposition of Block Copolymer Photosensitizer Based Formulations on Sugar Crystals This example demonstrates that the use of the micro thin film can be extended beyond lipids to any alternative carriers for hydrophobic photosensitizer drugs. The use of the micro-thin film technique for formulation of photosensitizer drug using block copolymer and deposition on sugar crystals resulted in a solid-state formulation that is easy to hydrate.

In this experiment the deposition of the photosensitizer BPD-MA with the block copolymer Pluronic® F127 onto the sugar lactose was examined. Formulations containing 5% (w/v) and a 10% (w/v) F127 were tested. 0.5 g lactose and 10 mg BPD-MA were added to two rotary evaporation flasks. A stock solution of 0.2 mg/ml F127 was prepared in $CH_2Cl_2$. 1.25 ml (for 5% w/v) and 2.5 ml (for 10% w/v) F127 stock solution was added to each flask. The final volume in each flask was made up to 5.0 ml with $CH_2Cl_2$ and the components mixed to ensure complete dissolution. The solvent was removed by rotary evaporation at 50° C., and the flask left under vacuum for a further 15 min at 23° C. Micro-thin film deposits were scraped from the walls and hydrated in 5 ml water at 50° C. The formulations were filtered twice using 0.2 µm syringe filters (Acrodisc, polysulphone).

It was observed that both the thin film formulations dissolved easily, particularly 5% w/v, which went into solution immediately on addition of water. Both the formulations (5% w/v and 10% w/v F127) filtered easily through 0.2 µm filters and with no drug loss.

The above example demonstrates that solid-state formulation of an A-ring photosensitizer and block copolymer carrier deposited on sugar crystals offers a very simple alternative to liposomal-based formulations. Furthermore, if prepared under sterile GMP conditions it can provide a simple, one step manufacturing process.

Example 16

Deposition of Block Copolymer Photosensitizer Based Formulations onto Sugar Crystals Using Ethanol as Solvent This experiment examines the substitution of ethanol for $CH_2Cl_2$ as the solvent for dissolving the block copolymer F127, and photosensitizer BPD-MA, for deposition on lactose crystals. It also examined the use of lower concentration of F127 for the formulation.

The experimental conditions and components were the same as Example 15 with the exception of the following changes. A stock of 0.2 mg/ml F127 was prepared in ethanol and 0.65 ml (2.5% w/v) and 1.25 ml (5% w/v) of the stock solution was added to two flasks. The final volume was made up to 5.0 ml with ethanol and the contents dissolved with warming. Ethanol was removed by rotary evaporation at 50° C., left under vacuum for 15 min at room. Micro-thin film deposits were scraped from the walls and dissolved in 5 ml water at 50° C. as previously described. Samples were filtered 3 times through 0.2 µm syringe filters.

Substitution of ethanol for $CH_2Cl_2$ as the solvent for dissolving and depositing the formulation on lactose crystals was successful. Both the 2.5% and 5% w/v of F127 formed micro-thin films after removal of ethanol, and were easily hydrated. Further these formulations were filtered through 0.2 µm filter with no resistance.

The above example demonstrates that ethanol can replace $CH_2Cl_2$ as the volatile solvent for dissolving block copolymer and A-ring photosensitizer for deposition on lactose sugar crystals.

Example 17

B-ring Photosensitizers Formulations Using Mixed Block Copolymers

This example illustrates the of blended block copolymers for dissolving and improving the hydration of B-ring photosensitizer solid support based formulations.

The poloxamer that was found to be useful in formulating a range of tetrapyrrolic drugs was Pluronic® P123, under the above conditions.

In this experiment formulation of B-ring photosensitizer, B-B3 at 2 mg/ml with blended P123 and F127 or PVP, using the thin film method as described in Example 15 were examined. The aim of the following experiment was to determine whether incorporation of solid compounds (e.g., PVP, F127) into the formulation might help to counteract the waxy nature of P123 in the thin film, hence improving hydration characteristics without destabilizing the formulation.

The polymer combinations used in this experiment are described in the following table. The relative ease of thin film hydration for each combination was observed. The drug concentration retention was determined by absorbance at t=0, 3 h and 24 h. Following centrifugation each sample was diluted to 1:100 dilution in MeOH and A690 measured.

The relative ease of hydration for the poloxamer or poloxamer combinations was observed to be as follows:

5% P123+5% F127>5% P123+5%PVP>10% P123+5%PVP>10% P123

P123 is semi solid and its waxy in nature makes it very difficult to hydrate. Based on the above results, formulations with a lower P123 content hydrated more readily. The presence of solid compounds such as PVP and F127 in combination with P123 facilitated the hydration of the formulations. Incorporation of crystalline lactose is advantageous because it resulted in the improvement of the quality of the thin film, which was drier and thinner and therefore easier to hydrate, compared to the previous poloxamer based thin films, which were then hydrated with iso-osmolar lactose solution.

The result of the drug retention measurement over time is shown in Table 12.

TABLE 12

B-B3 Retention In Various Polymeric Formulation Determined By Absorbance Readings (690 nm)

| Polymer Combination | $A_{690}$ | | |
| --- | --- | --- | --- |
| | T = 0 | T = 3 h | T = 24 h |
| 5% P123 + 5% F127 | 0.88 | 0.54 | 0.42 |
| | 0.93 | 0.57 | 0.45 |
| 5% P123 + 5% PVP | 0.84 | 0.75 | 0.57 |
| | 0.91 | 0.75 | 0.61 |
| 10% P123 + 5% PVP | 0.88 | 0.69 | 0.45 |
| | 0.89 | 0.71 | 0.44 |
| 10% P123 | 0.77 | 0.91 | 0.84 |
| | 0.81 | 0.91 | 0.79 |

The results show that all samples formulated in blended polymers lose drug on standing over 24 hours. It was observed that 10% P123 retained the most drug. The drug retention in the formulation after 24h was in the following order:

10% P123>10% P123+5% PVP>5% P123+5% PVP>5% P123+5% F127

These results indicate that the presence of P123 in the formulation allows for B-EA6 drug to be stable in the formulation. It has been previously shown that drug formulation with 10% w/v F127 resulted in poor formulation efficiency for B-EA6 (see Example 4 above). The use of various molecular weights of PVPs with the photosensitizer BPD-MA, also resulted in poor retention of the drug (results not shown).

The above example demonstrates that B-ring photosensitizer drug formulation and hydration is improved with blending of polymers and use of lactose. Pluronic P123, a block copolymer that is semi-solid and waxy at ambient temperatures, when blended with PVP or other block copolymers, such as Pluronic F127, which are solids, was shown to improves hydration of B-EA6 thin film preparation.

Example 18

Photosensitizers Formulations Using Mixed Block Copolymers and Dissolvable Crystalline Solid Support The objective of this experiment was to optimize the photosensitizer drug stability using different blends of copolymer content in the formulation while retaining the ease of hydration of the sugar based thin film. The effect of lyophilization of hydrated material was also examined.

Initially the aim was to incorporate 2 mg/ml of B-B3 into 10% w/v P123 by this method. It was shown in previous work that ~1.8 mg/ml B-B3 can typically be retained 24h post-hydration. This translates to approximately 10% drug loss. Unincorporated B-ring drugs undergo aggregation in aqueous solutions, which is characterized by appearance of a 730 nm absorbance peak. Although the formulations can be made completely aggregate free by centrifugation or sterile filtration through 0.2 μm filters, this adds another step in the manufacturing process, which can be avoided by increasing the copolymer:drug ratio.

In this experiment the B3-B was formulated using the sugar trehalose (9.5% w/v) to give a final drug concentration of 1 mg/mL. The non-blended and blended poloxamer contents of the test samples were as follows: 7.5% w/v P123; 9% w/v P123+1% w/v F127; and 10% w/v P123.

B-B3 was dissolved in $CH_2Cl_2$ to a concentration of 1 mg/nl, and I mL of the solution was dispensed into 25 ml round bottom flasks. A 100 mg/mL stock solution of Pluronic P123 in $CH_2Cl_2$ was prepared, and dispensed into the flasks, followed by solid F127 to give 7.5% w/v P123; 9% w/v P123+1% w/v F127; and 10% w/v P123, in duplicate. Trehalose was added to give 9.5% w/v final concentration in each of the flasks. Solvent was removed by rotary evaporation to give a micro-thin film composed of B3-B and copolymers deposited on trehalose crystals. The films were hydrated with distilled water (adjusted to pH 7.6) at room temperature. Hydrated samples were studied for stability at room temperature for up to 24 h by spectroscopic scanning between 650 and 750 nm following 1:100 dilution in water, pH 7.6. After 24 h stability studies, samples were lyophilized at −10° C.

The relative ease of reconstitution of the lyophilized formulations of the B-B3 with the various poloxamer combinations deposited on trehalose was observed to be as follows:

7.5% P123>9% P123+1% F127>10% P123

TABLE 13

Dependence of formulation stability on block copolymer content

| | Lyophilized Formulation $A_{690}$ Post Reconstitution (4 h) |
|---|---|
| 7.5% P123 | 0.308 |
| | 0.299 |
| 1% F127 + 9% P123 | 0.332 |
| | 0.382 |
| 10% P123 | 0.351 |
| | 0.342 |

These results once again suggests that the lower the content of the waxy copolymer (e.g. Pluronic P123), the greater the ease of hydration. In the previous example (Example 17) addition of 5% w/v solid copolymer (F127) into P123 was shown to cause destabilization of the formulation, however in the present experiment incorporation of 1% w/v resulted in superior hydration of the micro-thin film, without compromising formulation (Table 13).

The above example demonstrates that photosensitizers using blended poloxamers as carriers and depositing onto sugar results in stable solid-state formulations that are easier to hydrate, and retain the photosensitizer drug in a non-aggregated form.

Example 19

Photosensitizers Formulations Using Mixed Block Copolymers and Soluble Crystalline Solid Supports The following example demonstrates that complexes of photosensitizer drug blended copolymers P123 and F127 (lyophilized material) hydrate easier if trehalose is used as a solid support instead of lactose.

This experiment examined the use of blended block copolymers, 9% P123 and 1% F127 with 9.5% w/v lactose or trehalose, as solid supports for formulating 1 mg/ml B-B3. The control was 10% P123 with either 9.5% w/v lactose or trehalose. The procedure was carried out as described in Example 18 and the hydration of the thin film, or ease of reconstitution of the lyophilized preparations were examined. Formulations of B-B3 (1 mg/mL) with copolymer content of 10% P123 and 9% P123+1% F127 were prepared for comparison. Thin films were hydrated with 0.01M citrate-phosphate buffer pH 7.4. 1 mL of hydrated formulations was aliquoted into 2 mL lyophilization vials and lyophilized.

All the samples formed lyophilized cakes that were observed to be fluffy and uniform in appearance. The ease of hydration of lyophilized cakes were as follows:

9% P123+1% F127+trehalose>10% P123+trehalose>9% P123+1% F127+lactose>10% P123+lactose Increased ease of hydration may also be viewed as decreased times necessary for complete hydration.

Although all B-B3 formulation samples formed cakes upon lyophilization, formulations containing trehalose were surprisingly easier to reconstitute compared to lactose based formulations. This was irrespective of copolymer content.

The advantageous ease of hydrating, and thus decreased time for complete hydration, observed with trehalose containing formulations in comparison to lactose containing formulations is unexpected given the similarities between the two simple disaccharides. They would be expected to function similarly as solid supports, but trehalose use apparently provides an unexpected benefit for the hydration of medicament/carrier mixtures.

It was also confirmed that addition of solid copolymer, F127 to a concentration of 1% w/v resulted in easier reconstitution of the lyophilized cakes for both trehalose and lactose containing formulations.

Example 20

Preparation of Liposomes Using Thin Film Technology

The following example briefly describes the liposomal BPD-MA (Verteporfin, QLT PhotoTherapeutics Inc., Vancouver, BC) preparation by thin film technology using standard laboratory and large-scale manufacture to a final concentration of 2 mg/ml using:

For the standard laboratory preparation the liposomal bilayer components of 20 mg BPD-MA, 65 mg egg phosphatidyl glycerol (EPG) and 94 mg dimyristoyl phosphatidylcholine (DMPC), are combined in a round bottom flask and dissolved in 10 ml methylene dichloride ($CH_2Cl_2$). Dissolving 2 mg BPD-MA follows this. The solvent is removed using standard rotary evaporation (Rotavapor R-124 and Buchi B171 Vacobox pump) leaving a thin film of the bilayer components on the flask wall. Once the thin film is prepared, it is hydrated using 10 ml iso-osmolar lactose (10% w/v) to give a final concentration of 2 mg/ml BPD-MA. Size reduction is carried out by consecutive extrusions through 400 nm, 200 nm, and finally 100 nm pore polycarbonate membranes (5 times through each) under high pressure. Size distribution of the MLVs obtained after extrusion of the hydrated material was found to be bimodal with vesicles of diameter ranging from 120 to 140 nm and 50 to 60 nm, respectively. The final product was lyophilized and can be reconstituted prior to use by addition of water.

Large-scale preparation of liposomal BPD-MA is similar to that described above except for the following changes. The liposomal bilayer components include the lipids, BPD-MA and antioxidants, which are combined in a round bottom flask and dissolved in $CH_2Cl_2$. The solvent is removed using rotary evaporation leaving a thin film of the bilayer components on the flask wall. The thin film is hydrated using iso-osmolar lactose solution yielding MLVs. Size reduction of the hydrated material is carried out by homogenization and results in unilamellar vesicle, which are then filter sterilized prior to lyophilization.

Example 21

Micro-thin Film Procedure for Deposition of Lipids and Photosensitizer onto Crystalline Sugar The following example illustrates one embodiment of the invention using laboratory scale procedure for deposition of lipids and photosensitizer, BPD-MA, onto crystalline sugar, lactose. It results in a thin film composed of particulate lactose coated with the drug-lipid complex over a very high surface area. The micro-thin film can be scraped off the walls to give a powder which hydrates readily with water.

10 mg BPD-MA was combined with 32.5 mg phosphatidyl glycerol (EPG) and 47 mg dimyristoyl phosphatidylcholine (DMPC), and dissolved in 5 ml $CH_2Cl_2$. 2.5 ml of this solution (containing 5 mg BPD-MA) was then added to 250 g lactose in a rotary evaporator flask. The solvent was removed under rotary evaporation at 50° C. The film deposited on the glass wall was hydrated by addition of 2.5 ml warm distilled water (60° C.) with swirling. The hydrated material was examined under the microscope. Size reduction was carried out by extrusion of the hydrated material through 400, 200 and 100 nm pore polycarbonate membranes (5× through each) as described in Example 20.

Finely divided lactose, which is insoluble in organic solvents, was incorporated in particulate form into the thin film. It was observed that the BPD-MA/lipid coated lactose crystals were evenly deposited onto flask wall after rotary evaporation. The lactose thin film was readily removable and formed a powder when scraped from the glass wall. Hydration took place immediately upon addition of the distilled water and hand swirling. Examination of the solution under the microscope revealed well-hydrated spherical multilamellar vesicles (MLVs) and absence of crystals. Surprisingly the extrusion of the hydrated lactose MLV solution took place with exceptional ease compared to the conventional non-lactose thin film used previously (Example 20). Extrusion was carried out in 20 min in total compared to 2.5 h for MLVs derived from conventional thin film. This observation implies that the MLVs produced by hydration of the lactose thin film were relatively smaller than conventional ones.

The above suggests that the addition of a sugar, such as lactose, with the solvent prior to drying essentially results in a multitude of extremely thin "micro" films utilizing the entire surface area of the added solvent-insoluble particulate matter. Consequently, hydration of the films takes place very rapidly compared to the conventional film on glass. Additionally, this technique involving inclusion of lactose into the drug-lipid complex results in the formation of smaller MLVs as indicated by the ease of extrusion. This is advantageous for the manufacture of liposomal formulations, since phospholipids are highly susceptible to chemical degradation by hydrolysis arising from high local temperatures during homogenization. Therefore it is possible with this observation to reduce or use milder post-hydration processing for size reduction.

Example 22

Deposition of Lipids and Photosensitizer onto Crystalline Sugar: Use of Ethanol as a Solvent The following example shows that chlorinated solvents can be substituted with ethanol for depositing lipids and photosensitizer onto crystalline sugar using the micro-thin film technique.

In this experiment the effect of replacing $CH_2Cl_2$ with ethanol as a solvent for the sugar proliposomal formulation of photosensitizer and phospholipids was examined. The experiment was carried out as described in Example 21 except with the following changes: 20 mg BPD-MA was combined with 65 mg EPG and 94 mg DMPC, and dissolved in a total volume of 20 ml ethanol with occasional warming in 50° C. water bath. Ethanol was removed under rotary evaporation at 50° C., leaving BPD-MA/lipid coated lactose crystals evenly deposited onto flask wall. Flask was removed from the temperature bath, and left under vacuum for 10 min. The contents of the flask were scraped and hydrated by addition of 10 ml distilled water (60° C.) with swirling. The hydrated material was examined under the microscope and the MLV diameter was measured using laser light scattering on a NICOMP™ 370 Submicron Particle Sizer. Extrusion was then carried out as described in Example 20.

Microscopic examination of the hydrated material from the lactose thin film showed spherical MLVs with no evidence of unincorporated drug crystals. The mean diameter of the MLVs was 690 nm (92.44% by volume), which is smaller than obtained from hydration of the conventional thin films (>1 μm). Extrusion of the MLVs through the series of filters was very rapid compared to conventional MLVs. The final liposomes diameter following extrusion was found to be in a bimodal distribution similar to liposomes obtained by the conventional thin film method. The diameters of the unilamellar vesicles were found to be 110.4 nm (76.83% by volume) and 47.9 nm (23.17% by volume).

This again suggests that post hydration processing could be limited. As the size reduction procedure was the same in both the conventional thin film and the micro-thin film methods, it suggests that the multilamellar vesicles formed from hydration of the former were larger than the than those of the latter. This observation suggests that it is possible to reduce the processing intensity and/or time if the micro-thin film method was used.

The above example demonstrates successful replacement of chlorinated solvent with ethanol for the deposition of the drug-lipid complex onto sugar crystals, and confirms that smaller MLVs are formed using the micro-thin film technique.

Example 23

Deposition of Lipids and Photosensitizer onto Crystalline Sugar Using Ethanol: Use of Reduced Solvent Volume The following example illustrates that total volume of solvent required for dissolving the proliposome constituents can be decreased by dissolving the liposomal material before the photosensitizer.

The experimental procedure was carried out was as described in Example 22, with the exception of the following changes. The liposomal bilayer constituents, 32.5 mg of EPG and 47 mg of DMPC, were dissolved in 2 ml ethanol, instead of 20 ml. The solution was warmed to 50° C. in a water bath. This was followed by addition of 10 mg BPD-MA, and the total volume was made up to 4 ml to ensure complete dissolution (2.5 mg/ml final concentration). 0.5 g of lactose was added to the round bottom flask. The solvent was removed by rotary evaporation, and the flask removed from the water bath, and left under vacuum for 1.5 h. For hydration, 5 ml of pre-warmed distilled water (60° C.) was added to flask with swirling. Extrusion of the solution and sizing of the vesicles was carried out as described in Example 22.

The hydration of the lactose based micro-thin film took place readily. As previously observed, the extrusion of the hydrated material was rapid. Size determination of liposomes showed that a bimodal population of unilamellar vesicles was formed with mean diameters of 132.4 nm (70.5% by volume) and 58.4 nm (29.49% by volume). It was found that reduction in the volume of ethanol as a solvent did not significantly affect the final product of deposition of drug and lipids onto lactose crystals.

Example 24

Comparison of Conventional and Micro-thin Film Techniques for the Liposomal Formulation of the Photosensitizer Diethyleneglycol Ester A-ring (A-EA6)

The following example compares the conventional and micro-thin film formulation techniques for the preparation of liposomal A-ring photosensitizer, A-EA6.

The formulation of A-EA6 (NC0074, QLT PhotoTherapeutics Inc., Vancouver, BC) uses a drug to lipid ratio of 1:10 w/w where the lipid components are DMPC with 3% w/w dimyristoyl phosphatidylglycerol (DMPG). The experimental procedure was carried out as described in Example 21 but with the following changes:

20 mg A-EA6, 194 mg DMPC and 6 mg DMPG were added to a 250 mL round bottom flask and dissolved by addition of 10 mL $CH_2Cl_2$ containing 0.8% water. This was followed by addition of 0.92 g lactose powder. The $CH_2Cl_2$ was removed rapidly by rotary evaporation at 50° C., at maximum speed of rotation. Once a steady minimum pressure was achieved, the flask was held under vacuum for a further 20-30 min. The thin film was scraped off the walls and ground using a glass rod, and hydrated with 10 mL distilled water at 40° C. with hand swirling. A conventional thin film was prepared with the same drug and lipid composition, but without incorporation of lactose. It was hydrated with 9.2% w/v solution of lactose prewarmed to 40° C. MLVs from both hydrated thin films were examined under the microscope, and photographed.

It was observed that the EA6-A lactose micro-thin film hydrated very readily. Examination of the hydrated material under the microscope and using a hematocytometer showed MLVs of visibly smaller size than those from the conventional thin film. This was confirmed by size determination of the MLVs using an Accusizer (Model 770A) sizing systems (FIG. 1) which shows a smaller proportion of the larger MLVs in the micro-thin film preparation.

Example 25

Comparison of Conventional and Micro-thin Film Techniques for the Liposomal Formulation of the Photosensitizer A-EA6: Microfluidization The following example illustrates that microfluidisation is a better option than extrusion for transforming MLVs to unilamellar vesicles on a large scale.

MLVs obtained from each of the conventional and micro-thin films of EA6-A in 3% w/w DMPG/DMPC prepared in Example 24 were introduced into the reaction chamber of a small microfluidizer (23 ml capacity; M110S, Microfluidics). Each sample was microfludized using the suggested protocol from the manufacturer's operation manual. The reaction chamber was immersed in ice, with the pressure transducer (Dynisco μPR 690) setting adjusted to 10,000 psi.

Use of the microfluidizer required priming the system with 9.2% lactose. The dead volume retained was considerably higher than stated in the manual, and as a result, only ~2 mL of undiluted sample was recovered after the first pass in each case. As this volume was insufficient for further processing, it was pooled with material retained in the microfluidizer, which resulted in dilution of the formulation to 1 mg/mL in both batches. Processing was carried out for a total of 6 passes, with 200 μl samples being removed for particle sizing following every pass. Due to limited recovery and dilution of the above samples, 2 larger batches (20 mL) were prepared using the conventional thin film process, and microfluidized with a total of 5 passes. To avoid excessive dilution of the unilammelar vesicles, recovery was limited to 8 mL.

Microfluidisation was repeated with larger volumes of 20 mL. Hydration of conventional thin films still resulted in some dilution of the microfluidised sample. The final concentration of A-EA6 in both batches (HH02-5 A and HH02-5 B) was 1.5 mg/mL. These samples were processed with the microfluidiser in a hot water bath at 45° C. instead of ice to prevent suspension temperature falling below the phase transition of DMPC in between passes. Size determination was carried out by laser light scattering on a NICOMP™ 370 Submicron Particle Sizer.

Tables 14 and 15 show the results of size determination following each pass through the microfluidiser of hydrated conventional thin film and micro-thin film (10 mL batch), respectively.

TABLE 14

Microfluidization of conventional thin films[1]

| Pass Number | Temperature ° C. | Recovery (mL) | Size (nm) |
|---|---|---|---|
| 1 | 22 | 8.6 | — |
| 2 | 18 | 8 | — |
| 3 | 17 | 6.8 | 81 + 21[2] |
| 4 | 16.5 | 6 | 63 |
| 5 | 18 | 5.5 | 66 |
| 6 | 18 | 5 | 63 |

[1]10 mL batch
[2]2 populations

TABLE 15

Microfluidization of micro-thin films[1]

| Pass Number | Temperature ° C. | Recovery (mL) | Size (nm) |
|---|---|---|---|
| 1 | 16 | 9.8 | 141 + 54[2] |
| 2 | 15 | 10 | 62 |
| 3 | 15 | 9.5 | 67 |
| 4 | 15 | 9.4 | 59 |
| 5 | 16 | 9.4 | 60 |
| 6 | 16 | 8 | 57 |

[1]10 mL batch
[2]2 populations

For the smaller sized volume (10 mL) that was microfluidized, it was found that the A-EA6 vesicle size was ~60 nm. This size is considerably smaller than that which could be obtained by final extrusion through 100 nm filters (100-110 nm). Microfluidisation of the conventional thin film resulted in a single population following pass 4, whereas this was achieved at pass 2 for the micro-thin film sample. This latter population did not change with further processing, suggesting that it might indeed be possible to reduce MLV processing time if they were prepared using the micro-thin film method. Microfluidisation of the conventional and the micro-thin film with larger volumes of 20 mL resulted in mean vesicle size of 98 nm and 76 nm, respectively, after the first pass.

The above examples demonstrates that microfluidization of the conventional and micro-thin film formulations for the preparation of liposomal A-ring photosensitizer, A-EA6, is superior then extrusion technique for transforming MLVs to unilamellar vesicles.

Example 26

Comparison of Drug Release from Vesicles Formed from Conventional and Micro-thin Film Techniques This example illustrates the further advantages of using micro-thin film preparations over conventional thin film.

This experiment test drug release from micro-thin film preparations and conventional thin film vesicles (76 nm and 98 nm) produced in Example 25. The assay was carried out using an Aminco-Bowman 2 Fluorescence Spectrometer. It has previously been observed in the liposomal photosensitizer formulations that the fluorescence from the photosensitizer drug is quenched due to the high ratio of drug to lipid present. If other vehicles to which the drug can readily bind (e.g. plasma lipoproteins, fetal bovine serum (FB S), or even drug free liposomes) are added to a liposomal suspension, emission has been observed to increase in proportion to the amount of drug transferred to these vehicles. Fluorescence signal from liposomal suspensions is therefore low, and increases only when the drug leaves the bilayer for an alternative binding site.

The increase in fluorescence signal reflects liposomal drug transfer in proportion to the rate and extent of transfer to added serum components.

The liposomal suspension is diluted with 5% Dextrose to give an absorbance of 0.1 at the excitation wavelength (430 nm). Fluorescence from a liposomal suspension (2 mL) in a cuvette equilibrated to 23° C. gives the baseline fluorescence level ($F_o$); when a steady signal is achieved, the cuvette is removed from the holder. 100 μl of FBS is added to the cuvette, and increase in fluorescence is monitored (following a quick couple of inversions) over 2-3 min if necessary. Once a steady level is achieved (noted as $F_{fbs}$), the liposomal system is disrupted using 0.05% v/v Triton X-100 to get a 100% drug level. The maximum fluorescence level is noted as $F_{tx}$. The ratio of $F_{fbs}/F_{tx}$ gives an estimation of liposomal drug release, and is highly reproducible (SD ~0-2% for n=5). Reported release results are based on 2-5 repeat assays depending on instrumental stability.

Using the above release assay, it was found that drug release from liposomal A-EA6 to 5% FBS at (37° C.) of thin film and micro-thin film batches was 67% (±1.36, n=2) and 72% (±2.23, n=2), respectively. Based on this result it can be hypothesized that with the increase in surface area due to smaller vesicles, there will be a proportional increase in efficiency with which the photosensitizer drug is delivered to plasma components on injection. It has previously been observed that activity of photosensitizer drug in vivo is proportional to efficiency of delivery to serum, with various formulations tested.

Apart from the better drug delivery from smaller vesicles produced using the micro-thin film technique, there were additional advantages. On a large scale, all the solid formulation components can be combined in a single step and dissolved in the volatile solvent of choice in a closed system (with warming if necessary). The solvent can then be subsequently removed using existing large-scale spray drying equipment. Coating of particulate matter is also routinely carried out in the pharmaceutical industry using Fluid bed dispersion and Wurster column techniques. These techniques spray active materials in volatile organic solvents onto solid support particles suspended in the air. The final product can be hydrated conveniently and under controlled conditions in a single mixing vessel using water. These techniques have the potential for large-scale manufacture of injectable formulations, under sterile conditions. They are also far more reliable, controllable, reproducible, less time consuming in comparison to generation of numerous thin films, which are individually hydrated and pooled, for further processing for size reduction. Furthermore, hydration of the micro-thin films yields smaller MLVs, probably with lower lamellarity (number of concentric bilayers in MLVs), which might allow for reduction in microfluidisation time, as well as avoiding the additional manufacturing step of preparing a lactose solution for hydration.

Example 27

Hydrophilic and Hydrophobic BPD B-Ring Analogs

The following example illustrates benzoporphyrin derivatives (BPD) B ring analogs that may be used in this invention. The figure below illustrates the general chemical formula of BPD with X1, X2 and X3 representing different chemical groups. The various BPD B ring analogs produced with the differing groups X1, X2 and X3 are shown in Tables 16 and 17 as representative embodiments of the general structure depicted.

TABLE 16

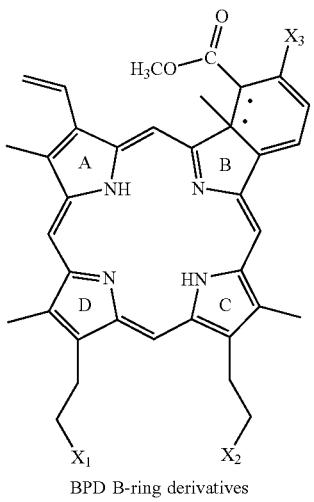

BPD B-ring derivatives

Hydrophilic BPD B-ring analogs.

| Drug | X1 | X2 | X3 |
|---|---|---|---|
| QLT0061 | COOH | COOH | COOH |
| QLT0077 | $CONH(CH_2)_2N^+(CH_3)_3I^-$ | $CONH(CH_2)_2N^+(CH_3)_3I^-$ | $COOCH_3$ |
| QLT0079 | $CONH(CH_2)_2N^+(CH_3)_2((CH_2)_3CH_3$ | $CONH(CH_2)_2N^+(CH_3)_2((CH_2)_3CH_3)$ | $COOCH_3$ |
| QLT0086[1] | $CONHCH(COOH)CH_2COOH$ | $CONHCH(COOH)CH_2COOH$ | $COOCH_3$ |
| QLT0092[2] | $CONH(CH_2)_2NH(CH_3)_2$ $CF_3COO^-$ | $CONH(CH_2)_2NH(CH_3)_2$ $CF_3COO—$ | $COOCH_3$ |
| QLT0094 | $CONHCH_2COOH$ | $CONHCH_2COOH$ | $CONHCH_2COOH$ |

[1] Batch contains trace amounts of $CF_3COO^-$.
[2] Batch contains 4 × ($CF_3COO^-$).

TABLE 17

Lipophilic BPD B-ring analogs.

| Drug | X1 | X2 | X3 |
|---|---|---|---|
| QLT0060 | $CO(O(CH_2)_2)OH$ | $CO(O(CH_2)_2)OH$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Example 28

Comparison of Tumor Recurrence in Mice Model Treated with PDT Using A- & B-ring Photosensitizers in Block Copolymer and Liposomal Formulations The following example illustrates that the efficiency of poloxamer based photosensitizer formulations over liposomal formulation in a tumor mouse model following PDT.

Photosensitizer formulations were prepared in 10% w/v Pluronics as described in Example 4. BPD-MA was formulated in F127. B-ring compounds B-EA6 and B-B3, were prepared in P123 due to insufficient drug loading in F127. Liposomal BPD-MA formulation was Verteporfin™ and B-ring compounds were formulated in the same lipid composition. Where DMSO/plasma preparations were made, the DMSO dissolved drug was added directly to mouse plasma and the drug association with different plasma components was observed.

In these experiments the tumor model used was the DBA/2 mouse (males) inoculated intradermally with M1 rhabdomyosarcoma tumor cells (M1, ATCC. When tumors reached a diameter of 4-6 mm, the mice (n=10, unless otherwise stated) were treated with photodynamic therapy (PDT). PDT involved intravenous injection of the formulated drug in 0.2 mL volume of PBS. This was followed by exposure of the tumor region to laser light (Argon pumped dye laser (5W), 690 nm, 50J/cm2) 15 min later. Animals were then monitored for tumor recurrence over a 20 day period post treatment.

Table 18. Results of Tumor Cure Following Administration of Poloxamer Formulations; Comparison to Liposomal BPD-MA

TABLE 18

Results of Tumor Cure Following Administration of Polaxamer Formulations; Comparison to Liposomal BPD-MA

| Photosensitizer/ Formulation Type | Photosensitizer Dosage | Percent (%) Mice Tumor Free | | |
|---|---|---|---|---|
| | | Day 7 | Day 14 | Day 20 |
| BPD-MA | | | | |
| Liposomal | 1.0 mg/kg | 100 | 100 | 30 |
| Pluronic F127 | 1.0 mg/kg | 100 | 60 | 60 |
| B-EA6 | | | | |
| Liposomal | 1.0 mg/kg | 90 | 70 | 60 |
| Pluronic P123 | 1.0 mg/kg | PT[1] | PT[1] | PT[1] |
| Pluronic P123 | 0.5 mg/kg | 80 | 60 | 40 |
| B-B3 | | | | |
| Liposomal | 1.0 mg/kg | 0[2] | —[2] | —[2] |
| Pluronic P123 | 1.0 mg/kg | 100 | 80 | 60 |
| Pluronic P123 | 1.2 mg/kg | 100[3] | 67[3] | 67[3] |
| Pluronic P123 | 1.25 mg/kg | 100 | 100 | 80 |

[1]Mice suffered from phototoxic (PT) reaction at the site of light exposure and were subsequently euthanized.
[2]n = 5, zero tumor cure, mice euthanized at day 7
[3]n = 3

Table 18 summarizes the result of the above experiments. The performance of B-ring compounds was compared to the liposomal BPD-MA (Verteporfin) formulation which was used as the standard for assessing performance of other photosensitizers and formulations. It was observed that at the end of the 20 day period, mice treated with the poloxamer formulation were twice as likely to remain tumor free compared to those treated with liposomal BPD-MA.

Although B-EA6 formulated poorly in liposomes (in terms of drug loading), it demonstrated the greatest potency of the three liposomal drugs tested in the mouse tumor model. Administration of the 1 mg/kg B-EA6, formulated in P123, to tumor bearing mice resulted in a strong phototoxic reaction (edema) at the irradiated site, and the animals were consequently euthanized. This observation suggested that better drug delivery is achieved using poloxamers compared to the liposomal formulations at the same drug dosage. At a lower dose of 0.5 mg/kg, a cure rate was achieved similar to that of liposomal formulations of B-EA6 and BPD-MA at 1 mg/kg.

B-B3 demonstrated greatest sensitivity to the drug delivery agent (or "carrier") used in the formulation. At these levels, the plasma /DMSO preparation was found to be completely ineffective for PDT purposes. One of the most important modes of action of PDT is the disruption of neovasculature. Performance of B-B3 formulated in P123 at 1 mg/ml was marginally better than that of liposomal BPD-MA, and comparable to BPD-MA in poloxamer formulations. Increasing the dose B-B3 by 25% resulted in a marked improvement in performance in the tumor assay.

The results show that B-ring compounds formulated in poloxamers such Pluronic P123 enhanced performance of PDT in vivo. Without being bound by theory, the observed effects could be attributed partly to facilitation of the drugs across cellular membranes by the poloxamer and partly to improved delivery of drug to plasma lipoproteins. Although both B-ring compounds EA6 and B-3 had a tendency to aggregate, it was the amount associated with the lipoprotein fraction that dictated the efficacy of PDT in vivo. B-B3 showed poor delivery to the lipoprotein fraction for both liposomal and DMSO/plasma formulations (Table 9) and this resulted in failure of PDT in the tumor model. On the other hand, in the case of liposomal and Pluronic formulation of B-EA6, delivery to lipoproteins was equivalent (Table 10), the results in vivo were not markedly different.

Furthermore, when comparing liposomal and poloxamer formulations of B ring compounds, a lower concentration of the photosensitizer in the poloxamer formulations appears to give similar results to those in the liposomal preparations. In fact, excessive photosensitivity at the irradiated site when using B-EA6 at the dose traditionally used for liposomal BPD-MA suggests that the drug dosage for achieving good PDT response can be considerably lowered. The above example demonstrates that block copolymers allow formulation and potential use of B-ring compounds (which were found ineffective or difficult to formulate in liposomes or homopolymers) to give photosensitizer products with greatly enhanced drug delivery characteristics.

The above examples demonstrate the advantages of blended and non-blended block copolymers of different characteristics for formulation of hydrophobic photosensitizers and maintaining them in non-aggregated form prior to use. It also illustrates the advantages of solid-substrates and especially crystalline sugars for facilitating hydration and reconstitution of photosensitizer formulations. The solid-support has also been found to be advantageous for use in formulations of photosensitizers that do not aggregate in the lipid fraction of liposomes.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A dried photosensitizer-carrier composition, consisting essentially of:
   (a) a mixture of a polypyrrolic macrocyclic photosensitizer and at least one triblock copolymer carrier agent selected from a group consisting of poloxamer 403 (P123), poloxamer 407 (F127), poloxamer 402 (L122), poloxamer 181 (L61), poloxamer 401, (L121) and poloxamer 185 (P65); and
   (b) at least one solid endo support physically associated with said mixture; wherein said composition forms a complex between said photosensitizer and said carrier upon hydration with an aqueous medium, said complex is in the form-selected from the group consisting of micelles, vesicles, emulsion, gel and matrix.

2. The composition of claim 1 wherein said composition forms, upon hydration with an aqueous based medium, a complex that is micellar.

3. A method for formulating a dried mixture of photosensitizer and carrier agent, consisting essentially of the steps of:
   (a) mixing together a polypyrrolic macrocyclic photosensitizer and at least one triblock copolymer carrier agent selected from a group consisting of poloxamer 403 (P123), poloxamer 407 (F127), poloxamer 402 (L122), poloxamer 181 (L61), poloxamer 401, (L121) and poloxamer 185 (P65) in contact with at least one solid endo support; and
   (b) physically associating the mixture of photosensitizer and carrier agent with said solid endo support upon drying said mixture; wherein said mixture forms a complex between said photosensitizer and said carrier upon hydration with an aqueous medium, said complex is in the form selected from the group consisting of micelles, vesicles, emulsion, gel and matrix.

4. The method of claim 3 wherein said carrier agent in liquid form comprises the carrier dissolved in an organic solvent.

5. The method of claim 4 wherein said solvent is volatile.

6. The composition of claim 1 wherein said endo support is soluble or hydratable in an aqueous based medium.

7. The composition of claim 6 wherein said endo support is selected from the group consisting of a monosaccharide, disaccharide, aminoglycoside, and derivatives thereof.

8. The composition of claim 7 wherein the disaccharide is selected from the group consisting of maltose, lactose, sucrose and trehalose.

9. The composition of claim 1 wherein said photosensitizer is selected from the group consisting of porphyrins, pyrroles, tetrapyrrolic compounds, expanded pyrrolic macrocycles and their derivatives.

10. The composition of claim 9 wherein said porphyrin derivative is selected from the group consisting of green porphyrins, tetrahydrochlorins, chlorins bacteriochlorins, isobacteriochlorins, pyropheophorbides, purpurins, texaphyrins, phenothiaziniums, phthalocyanines, naphthalocyanines, porphycenes, pheophorbides, sapphyrins and texaphyrins.

11. The composition of claim 10 wherein said green porphyrin is selected from the group consisting of benzoporphyrin derivatives (BPD).

12. The composition of claim 11 wherein said BPD is selected from a group consisting of A ring, B ring, C ring, and D ring derivatives.

13. The composition of claim 12 wherein said BPD ring derivative is selected from a group consisting of benzoporphyrin derivative monoacid ring A (BPD-MA), A-EA6, A-B3, benzoporphyrin derivative monoacid ring B (BPD-MB), B-EA6, and B-B3.

14. The composition of claim 1 wherein said endo-support is non-hydratable in an aqueous based medium.

15. The composition of claim 14 wherein said endo-support is a polymeric compound.

16. The method of claim 14 wherein said endo-support is removed after hydration of the photosensitizer-carrier mixtured. medium, and wherein said endo-support removed after hydration of the photosensitizer-carrier mixture.

17. The composition of claim 1 wherein said carrier agent is poloxamer 403.

18. The composition of claim 17 wherein said triblock copolymer carrier is selected from the group consisting of symmetric A-B-A and non-symmetric A-B-A' triblock copolymers.

19. The composition of claim 18 wherein said triblock copolymer is polyoxyethylene polyoxypropylene block copolymer of the formula $HO(C_2H_4O)_a(C_3H_6O)_b(C_2H_4O)_cH$, where a and c are independently 1-150 units and b=10-200 units with the overall molecular weight ranging from 1,000 to 50,000 daltons.

20. The composition of claim 19 wherein said triblock copolymer is selected from a group consisting of poloxamers wherein a=c=1 to 150 units and b=10-200 units.

21. A method of preparing a hydrated photosensitizer-carrier complex comprising preparing a dried mixture of photosensitizer and carrier agent by the method of claim 4 and hydrating said mixture of photo sensitizer and carrier agent with an aqueous based medium to produce a hydrated photosensitizer-carrier complex.

22. The method of claim 21 wherein said complex is micellar.

23. The method of claim 21 wherein said hydrated mixture of photosensitizer, carrier, and endo support is further processed to a reduced size or further formulated.

24. A method for conducting photodynamic therapy comprising: administering a photosensitizer and copolymer complex produced by hydration of the composition of claim 1 to a subject in need of photodynamic therapy; and irradiating said subject to activate said photosensitizer.

* * * * *